(12) United States Patent
Hirokawa et al.

(10) Patent No.: US 12,396,642 B2
(45) Date of Patent: Aug. 26, 2025

(54) IMAGE PROCESSING METHOD, IMAGE PROCESSING DEVICE, AND PROGRAM

(71) Applicant: NIKON CORPORATION, Tokyo (JP)

(72) Inventors: Mariko Hirokawa, Yokohami (JP); Yasushi Tanabe, Fujisawa (JP)

(73) Assignee: NIKON CORPORATION, Tokyo (JP)

( * ) Notice: Subject to any disclaimer, the term of this patent is extended or adjusted under 35 U.S.C. 154(b) by 168 days.

(21) Appl. No.: 17/769,305

(22) PCT Filed: Oct. 15, 2019

(86) PCT No.: PCT/JP2019/040482
§ 371 (c)(1),
(2) Date: Apr. 14, 2022

(87) PCT Pub. No.: WO2021/074961
PCT Pub. Date: Apr. 22, 2021

(65) Prior Publication Data
US 2024/0215823 A1    Jul. 4, 2024

(51) Int. Cl.
*A61B 3/12* (2006.01)
*G06T 7/00* (2017.01)
*G06T 7/11* (2017.01)
*G06T 7/13* (2017.01)
*G06V 40/18* (2022.01)

(52) U.S. Cl.
CPC .............. *A61B 3/12* (2013.01); *G06T 7/0012* (2013.01); *G06T 7/11* (2017.01); *G06T 7/13* (2017.01); *G06V 40/193* (2022.01); *G06T 2207/30041* (2013.01); *G06T 2207/30101* (2013.01)

(58) Field of Classification Search
CPC .......... A61B 3/12; A61B 3/14; G06T 7/0012; G06T 7/11; G06T 7/13; G06T 2207/30041; G06T 2207/30101; G06T 7/136; G06T 7/155; G06V 40/193
USPC ....................................................... 351/206
See application file for complete search history.

(56) References Cited

U.S. PATENT DOCUMENTS

| | | | |
|---|---|---|---|
| 2008/0007691 A1* | 1/2008 | Mihashi | G06T 7/33 351/206 |
| 2014/0303013 A1* | 10/2014 | Hageman | A61K 31/225 506/9 |
| 2021/0004939 A1 | 1/2021 | Hirokawa | |
| 2021/0027476 A1* | 1/2021 | Hirokawa | G06T 3/18 |
| 2021/0035294 A1* | 2/2021 | Tanabe | A61B 3/0025 |
| 2023/0130244 A1* | 4/2023 | Hirokawa | A61B 5/02007 382/128 |

FOREIGN PATENT DOCUMENTS

WO    WO-2019/181981 A1    9/2019

OTHER PUBLICATIONS

Office Action of corresponding Japanese Patent Application No. 2021-552010, dated Jan. 10, 2023.
(Continued)

*Primary Examiner* — Mohammed A Hasan
(74) *Attorney, Agent, or Firm* — Foley & Lardner LLP

(57) ABSTRACT

A processor acquires a fundus image, generates a choroidal vascular image from the fundus image, and detects a watershed of a choroidal vascular network in the choroidal vascular image.

21 Claims, 22 Drawing Sheets

(56) References Cited

OTHER PUBLICATIONS

Sonoda, Shozo, The Council Designated Lectures I of the 122nd Annual Meeting of the Japanese Ophthalmological Society, "Bioimaging and Ocular Pathology, Introducing Timelines to Imaging Analysis : Quantitative Analysis of Retinochoroidal Disease Using Imaging Technology", Journal of Japanese Ophthalmological Society, Mar. 10, 2019, vol. 123, No. 3, pp. 260-283, with partial translation, 26 pages.

\* cited by examiner

IMAGE PROCESSING METHOD, IMAGE PROCESSING DEVICE, AND PROGRAM

TECHNICAL FIELD

The technology disclosed relates to an image processing method, an image processing device, and a program.

BACKGROUND ART

The specification of U.S. Pat. No. 8,636,364 discloses identifying positions of vortex veins from a fundus image.

There is a demand for technology to analyze choroidal blood vessels from a fundus image.

SUMMARY OF INVENTION

An image processing method of a first aspect of technology disclosed herein including, a processor acquiring a fundus image, the processor generating a choroidal vascular image from the fundus image, and the processor detecting a watershed of a choroidal vascular network in the choroidal vascular image.

An image processing device of a second aspect of technology disclosed herein including, a memory, and a processor coupled to the memory, wherein the processor, acquires a fundus image, generates a choroidal vascular image from the fundus image, and detects a watershed of a choroidal vascular network in the choroidal vascular image.

A program of a third aspect of technology disclosed herein causes a computer to execute processing including, acquiring a fundus image, generating a choroidal vascular image from the fundus image, and detecting a watershed of a choroidal vascular network in the choroidal vascular image.

DESCRIPTION OF EMBODIMENTS

Detailed explanation follows regarding exemplary embodiments of the present invention, with reference to the drawings.

Figure 1:
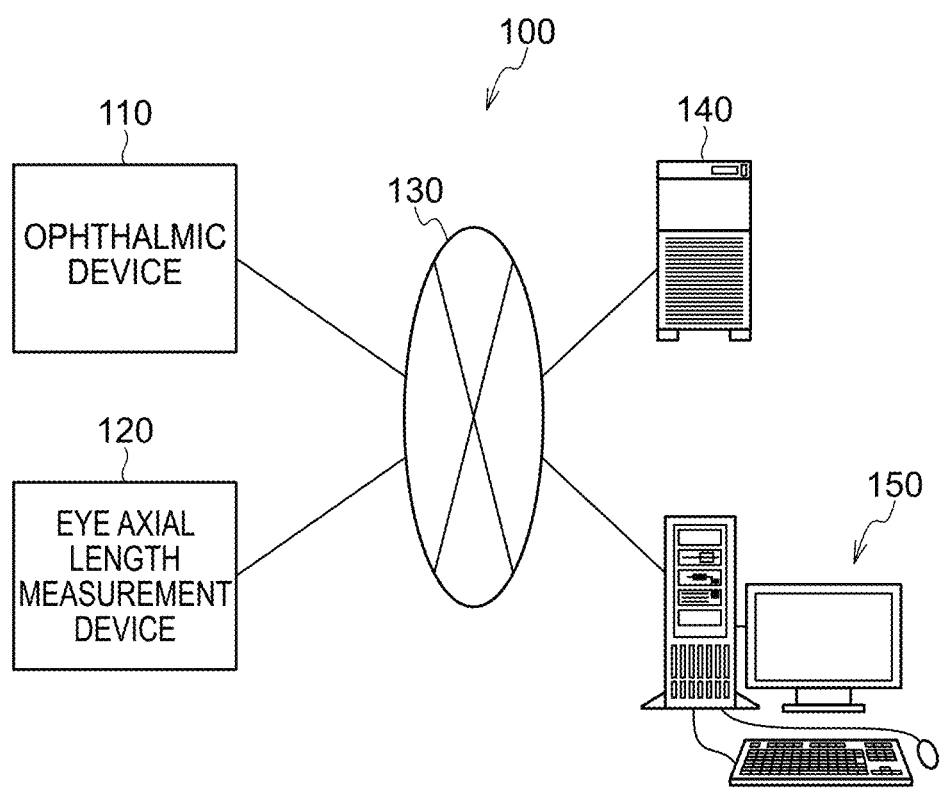
FIG. 1 is a block diagram of an ophthalmic system 100.

Explanation follows regarding a configuration of an ophthalmic system 100, with reference to FIG. 1. As illustrated in FIG. 1, the ophthalmic system 100 includes an ophthalmic device 110, an eye axial length measurement device 120, a management server device (referred to hereafter as "server") 140, and an image display device (referred to hereafter as "viewer") 150. The ophthalmic device 110 acquires an image of the fundus. The eye axial length measurement device 120 measures the axial length of the eye of a patient. The server 140 stores fundus images that were obtained by imaging the fundus of patients using the ophthalmic device 110 in association with patient IDs. The viewer 150 displays medical information such as fundus images acquired from the server 140.

The server 140 is an example of an "image processing device" of technology disclosed herein.

The ophthalmic device 110, the eye axial length measurement device 120, the server 140, and the viewer 150 are connected together through a network 130.

Figure 2:
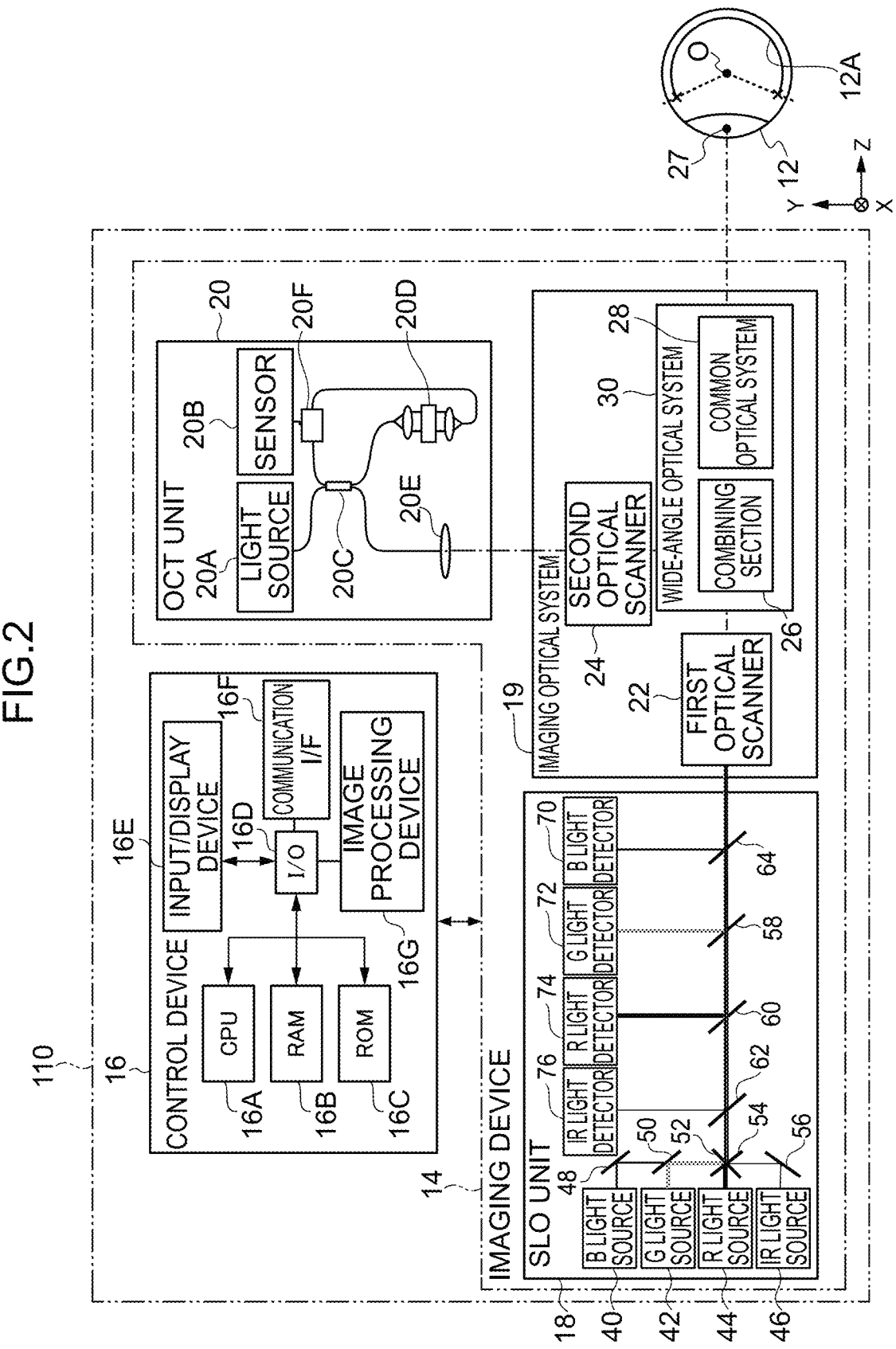
FIG. 2 is a schematic configuration diagram illustrating an overall configuration of an ophthalmic device 110.

Next, explanation follows regarding a configuration of the ophthalmic device 110, with reference to FIG. 2.

For ease of explanation, scanning laser ophthalmoscope is abbreviated to SLO. Optical coherence tomography is also abbreviated to OCT.

With the ophthalmic device 110 installed on a horizontal plane and a horizontal direction taken as an X direction, a direction perpendicular to the horizontal plane is denoted a Y direction, and a direction connecting the center of the pupil at the anterior eye portion of the examined eye 12 and the center of the eyeball is denoted a Z direction. The X direction, the Y direction, and the Z direction are thus mutually perpendicular directions.

The ophthalmic device 110 includes an imaging device 14 and a control device 16. The imaging device 14 is provided with an SLO unit 18, an OCT unit 20, and an imaging optical system 19, and acquires a fundus image of the fundus of the examined eye 12. Two-dimensional fundus images that have been acquired by the SLO unit 18 are referred to hereafter as SLO images. Tomographic images, face-on images (en-face images) and the like of the retina created based on OCT data acquired by the OCT unit 20 are referred to hereafter as OCT images.

The control device 16 includes a computer provided with a Central Processing Unit (CPU) 16A, Random Access Memory (RAM) 16B, Read-Only Memory (ROM) 16C, and an input/output (I/O) port 16D.

The control device 16 is provided with an input/display device 16E connected to the CPU 16A through the I/O port 16D. The input/display device 16E includes a graphical user interface to display images of the examined eye 12 and to receive various instructions from a user. An example of the graphical user interface is a touch panel display.

The control device 16 is also provided with an image processing device 16G connected to the I/O port 16D. The image processing device 16G generates images of the examined eye 12 based on data acquired by the imaging device 14. The control device 16 is provided with a communication interface (I/F) 16F connected to the I/O port 16D. The ophthalmic device 110 is connected to the eye axial length measurement device 120, the server 140, and the viewer 150 through the communication interface (I/F) 16F and the network 130.

Although the control device 16 of the ophthalmic device 110 is provided with the input/display device 16E as illustrated in FIG. 2, the technology disclosed herein is not limited thereto. For example, a configuration may adopted in which the control device 16 of the ophthalmic device 110 is not provided with the input/display device 16E, and instead a separate input/display device is provided that is physically independent of the ophthalmic device 110. In such cases, the display device is provided with an image processing processor unit that operates under the control of the CPU 16A in the control device 16. Such an image processing processor unit may display SLO images and the like based on an image signal output as an instruction by the CPU 16A.

The imaging device 14 operates under the control of the CPU 16A of the control device 16. The imaging device 14 includes the SLO unit 18, an imaging optical system 19, and the OCT unit 20. The imaging optical system 19 includes a first optical scanner 22, a second optical scanner 24, and a wide-angle optical system 30.

The first optical scanner 22 scans light emitted from the SLO unit 18 two dimensionally in the X direction and the Y direction. The second optical scanner 24 scans light emitted from the OCT unit 20 two dimensionally in the X direction and the Y direction. As long as the first optical scanner 22 and the second optical scanner 24 are optical elements capable of deflecting light beams, they may be configured by any out of, for example, polygon mirrors, mirror galvanometers, or the like. A combination thereof may also be employed.

The wide-angle optical system 30 includes an objective optical system (not illustrated in FIG. 2) provided with a common optical system 28, and a combining section 26 that combines light from the SLO unit 18 with light from the OCT unit 20.

The objective optical system of the common optical system 28 may be a reflection optical system employing a concave mirror such as an elliptical mirror, a refraction optical system employing a wide-angle lens, or may be a reflection-refraction optical system employing a combination of a concave mirror and a lens. Employing a wide-angle optical system that utilizes an elliptical mirror, wide-angle lens, or the like enables imaging to be performed not only of a central portion of the fundus where the optic nerve head and macula are present, but also of the retina at the periphery of the fundus where an equatorial portion of the eyeball and vortex veins are present.

For a system including an elliptical mirror, a configuration may be adopted that utilizes an elliptical mirror system as disclosed in International Publication (WO) Nos. 2016/103484 or 2016/103489. The disclosures of WO Nos. 2016/103484 and 2016/103489 are incorporated in their entirety by reference herein.

Observation of the fundus over a wide field of view (FOV) 12A is implemented by employing the wide-angle optical system 30. The FOV 12A refers to a range capable of being imaged by the imaging device 14. The FOV 12A may be expressed as a viewing angle. In the present exemplary embodiment the viewing angle may be defined in terms of an internal illumination angle and an external illumination angle. The external illumination angle is the angle of illumination by a light beam shone from the ophthalmic device 110 toward the examined eye 12, and is an angle of illumination defined with respect to a pupil 27. The internal illumination angle is the angle of illumination of a light beam shone onto the fundus, and is an angle of illumination defined with respect to an eyeball center O. A correspondence relationship exists between the external illumination angle and the internal illumination angle. For example, an external illumination angle of 120° is equivalent to an internal illumination angle of approximately 160°. The internal illumination angle in the present exemplary embodiment is 200°.

An angle of 200° for the internal illumination angle is an example of a "specific value" of technology disclosed herein.

SLO fundus images obtained by imaging at an imaging angle having an internal illumination angle of 160° or greater are referred to as UWF-SLO fundus images. UWF is an abbreviation of ultra-wide field.

An SLO system is realized by the control device 16, the SLO unit 18, and the imaging optical system 19 as illustrated in FIG. 2. The SLO system is provided with the wide-angle optical system 30, enabling fundus imaging over the wide FOV 12A.

The SLO unit 18 is provided with plural light sources such as, for example, a blue (B) light source 40, a green (G) light source 42, a red (R) light source 44, an infrared (for example near infrared) (IR) light source 46, and optical systems 48, 50, 52, 54, 56 to guide the light from the light sources 40, 42, 44, 46 onto a single optical path using reflection or transmission. The optical systems 48, 50, 56 are configured by mirrors, and the optical systems 52, 54 are configured by beam splitters. B light is reflected by the optical system 48, is transmitted through the optical system 50, and is reflected by the optical system 54. G light is reflected by the optical systems 50, 54, R light is transmitted through the optical systems 52, 54, and IR light is reflected by the optical systems 56, 52. The respective lights are thereby guided onto a single optical path.

The SLO unit 18 is configured so as to be capable of switching between the light source or the combination of light sources employed for emitting laser light of different wavelengths, such as a mode in which G light, R light and B light are emitted, a mode in which infrared light is emitted, etc. Although the example in FIG. 2 includes four light sources, i.e. the B light source 40, the G light source 42, the R light source 44, and the IR light source 46, the technology disclosed herein is not limited thereto. For example, the SLO unit 18 may, furthermore, also include a white light source, in a configuration in which light is emitted in various modes, such as a mode in which white light is emitted alone.

Light introduced to the imaging optical system 19 from the SLO unit 18 is scanned in the X direction and the Y direction by the first optical scanner 22. The scanning light passes through the wide-angle optical system 30 and the pupil 27 and is shone onto the posterior eye portion of the examined eye 12. Reflected light that has been reflected by the fundus passes through the wide-angle optical system 30) and the first optical scanner 22 and is introduced into the SLO unit 18.

The SLO unit 18 is provided with a beam splitter 64 that, from out of the light coming from the posterior eye portion (e.g. fundus) of the examined eye 12, reflects the B light therein and transmits light other than B light therein, and a beam splitter 58 that, from out of the light transmitted by the beam splitter 64, reflects the G light therein and transmits light other than G light therein. The SLO unit 18 is further provided with a beam splitter 60 that, from out of the light transmitted through the beam splitter 58, reflects R light therein and transmits light other than R light therein. The SLO unit 18 is further provided with a beam splitter 62 that reflects IR light from out of the light transmitted through the beam splitter 60.

The SLO unit 18 is provided with plural light detectors corresponding to the plural light sources. The SLO unit 18 includes a B light detector 70 for detecting B light reflected by the beam splitter 64, and a G light detector 72 for detecting G light reflected by the beam splitter 58. The SLO unit 18 includes an R light detector 74 for detecting R light reflected by the beam splitter 60 and an IR light detector 76 for detecting IR light reflected by the beam splitter 62.

Light that has passed through the wide-angle optical system 30 and the first optical scanner 22 and been introduced into the SLO unit 18 (i.e. reflected light that has been reflected by the fundus) is reflected by the beam splitter 64 and photo-detected by the B light detector 70 when B light, and is transmitted through the beam splitter 64 and reflected by the beam splitter 58 and photo-detected by the G light detector 72 when G light. When R light, the incident light is transmitted through the beam splitters 64, 58, reflected by the beam splitter 60, and photo-detected by the R light detector 74. When IR light, the incident light is transmitted through the beam splitters 64, 58, 60, reflected by the beam splitter 62, and photo-detected by the IR light detector 76. The image processing device 16G that operates under the control of the CPU 16A employs signals detected by the B light detector 70, the G light detector 72, the R light detector 74, and the IR light detector 76 to generate UWF-SLO images.

The UWF-SLO image (sometimes referred to as a UWF fundus image or an original fundus image as described below) encompasses a UWF-SLO image (green fundus image) obtained by imaging the fundus in green, and a UWF-SLO image (red fundus image) obtained by imaging the fundus in red. The UWF-SLO image further encompasses a UWF-SLO image (blue fundus image) obtained by imaging the fundus in blue, and a UWF-SLO image (IR fundus image) obtained by imaging the fundus in IR.

The control device 16 also controls the light sources 40, 42, 44 so as to emit light at the same time. A green fundus image, a red fundus image, and a blue fundus image are obtained with mutually corresponding positions by imaging the fundus of the examined eye 12 at the same time with the B light, G light, and R light. An RGB color fundus image is obtained from the green fundus image, the red fundus image, and the blue fundus image. The control device 16 obtains a green fundus image and a red fundus image with mutually corresponding positions by controlling the light sources 42, 44 so as to emit light at the same time and imaging the fundus of the examined eye 12 at the same time with the G light and R light. An RG color fundus image is obtained from the green fundus image and the red fundus image.

Specific examples of the UWF-SLO image include a blue fundus image, a green fundus image, a red fundus image, an IR fundus image, an RGB color fundus image, and an RG color fundus image. The image data for the respective UWF-SLO images are transmitted from the ophthalmic device 110 to the server 140 through the communication interface (I/F) 16F, together with patient information input through the input/display device 16E. The respective image data of the UWF-SLO image and the patient information is stored associated with each other in the storage device 254. The patient information includes, for example, patient ID, name, age, visual acuity, right eye/left eye discriminator, and the like. The patient information is input by an operator through the input/display device 16E.

An OCT system is realized by the control device 16, the OCT unit 20, and the imaging optical system 19 illustrated in FIG. 2. The OCT system is provided with the wide-angle optical system 30. This enables fundus imaging to be performed over the wide FOV 12A similarly to when imaging the SLO fundus images as described above. The OCT unit 20 includes a light source 20A, a sensor (detector) 20B, a first light coupler 20C, a reference optical system 20D, a collimator lens 20E, and a second light coupler 20F.

Light emitted from the light source 20A is split by the first light coupler 20C. After one part of the split light has been collimated by the collimator lens 20E into parallel light, to serve as measurement light, the parallel light is introduced into the imaging optical system 19. The measurement light is scanned in the X direction and the Y direction by the second optical scanner 24. The scanning light is shone onto the fundus through the wide-angle optical system 30 and the pupil 27. Measurement light that has been reflected by the fundus passes through the wide-angle optical system 30 and the second optical scanner 24 so as to be introduced into the OCT unit 20. The measurement light then passes through the collimator lens 20E and the first light coupler 20C before being incident to the second light coupler 20F.

The other part of the light emitted from the light source 20A and split by the first light coupler 20C is introduced into the reference optical system 20D as reference light, and is made incident to the second light coupler 20F through the reference optical system 20D.

The respective lights that are incident to the second light coupler 20F, namely the measurement light reflected by the fundus and the reference light, interfere with each other in the second light coupler 20F so as to generate interference light. The interference light is photo-detected by the sensor 20B. The image processing device 16G operating under the control of the CPU 16A generates OCT images, such as tomographic images and en-face images, based on OCT data detected by the sensor 20B.

OCT fundus images obtained by imaging at an imaging angle having an internal illumination angle of 160° or greater are referred to as UWF-OCT images.

The image data of the UWF-OCT images is transmitted, together with the patient information, from the ophthalmic device 110 to the server 140 though the communication interface (I/F) 16F. The image data of the UWF-OCT images and the patient information is stored associated with each other in the storage device 254.

Note that although in the present exemplary embodiment an example is given in which the light source 20A is a swept-source OCT (SS-OCT), the light source 20A may be configured from various types of OCT system, such as a spectral-domain OCT (SD-OCT) or a time-domain OCT (TD-OCT) system.

Next, explanation follows regarding the eye axial length measurement device 120. The eye axial length measurement device 120 has two modes, i.e. a first mode and a second mode, for measuring eye axial length, this being the length of an examined eye 12 in an eye axial direction. In the first mode light from a non-illustrated light source is guided into the examined eye 12. Interference light between light reflected from the fundus and light reflected from the cornea is photo-detected, and the eye axial length is measured based on an interference signal representing the photo-detected interference light. The second mode is a mode to measure the eye axial length by employing non-illustrated ultrasound waves.

The eye axial length measurement device 120 transmits the eye axial length as measured using either the first mode or the second mode to the server 140. The eye axial length may be measured using both the first mode and the second mode, and in such cases, an average of the eye axial lengths as measured using the two modes is transmitted to the server 140 as the eye axial length. The server 140 stores the eye axial length of the patients in association with patient ID.

Figure 3:
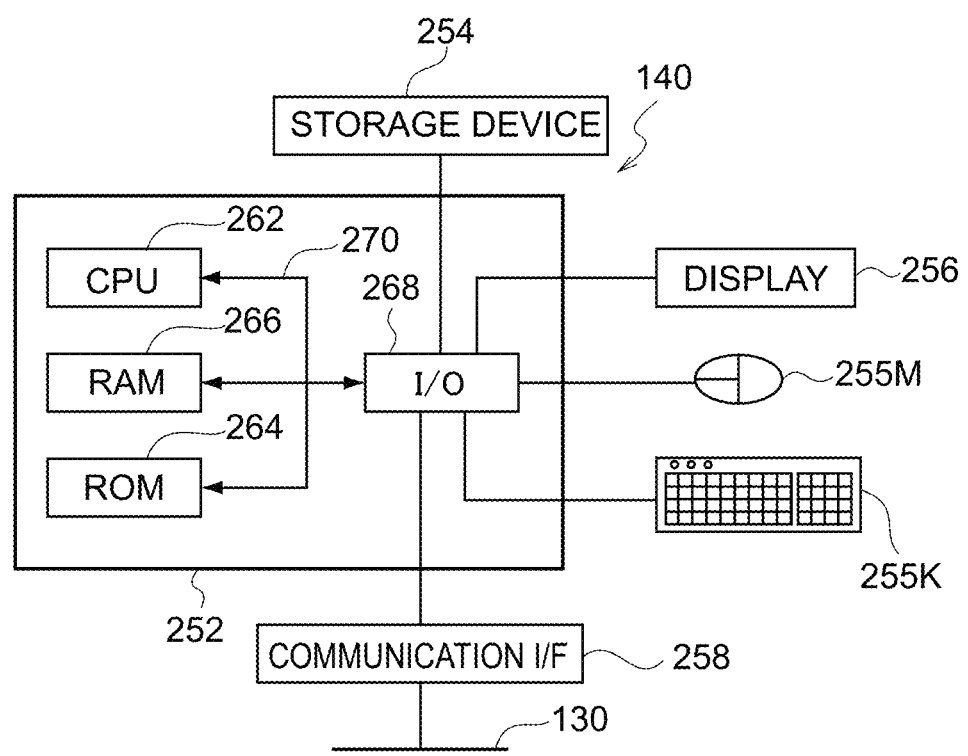
FIG. 3 is a block diagram of configuration of an electrical system of a server 140.

Explanation follows regarding a configuration of an electrical system of the server 140, with reference to FIG. 3. As illustrated in FIG. 3, the server 140 is provided with a computer body 252. The computer body 252 includes a CPU 262, RAM 266, ROM 264, and an input/output (I/O) port 268 connected together by a bus 270. The storage device 254, a display 256, a mouse 255M, a keyboard 255K, and a communication interface (I/F) 258 are connected to the input/output (I/O) port 268. The storage device 254 is, for example, configured by non-volatile memory. The input/output (I/O) port 268 is connected to the network 130 through the communication interface (I/F) 258. The server 140 is thus capable of communicating with the ophthalmic device 110 and the viewer 150. The storage device 254 is stored with an image processing program, described later. Note that the image processing program may be stored in the ROM 264.

The image processing program is an example of a "program" of technology disclosed herein. The storage device 254 and the ROM 264 are examples of "memory" and "computer readable storage medium" of technology disclosed herein. The CPU 262 is an example of a "processor" of technology disclosed herein.

A processing section 210, described later, of the server 140 (see also FIG. 5) stores various data received from the ophthalmic device 110 in the storage device 254. More specifically, the processing section 210 stores respective image data of the UWF-SLO images and image data of the UWF-OCT images in the storage device 254 associated with the patient information (such as the patient ID as described above). Moreover, in cases in which there is a pathological change in the examined eye of the patient and cases in which surgery has been performed to a pathological lesion, pathology information is input through the input/display device 16E of the ophthalmic device 110 and transmitted to the server 140. The pathology information is stored in the storage device 254 associated with the patient information. The pathology information includes information about the position of the pathological lesion, name of the pathological change, and name of the surgeon and date/time of surgery etc. when surgery was performed on the pathological lesion.

The viewer 150 is provided with a computer equipped with a CPU, RAM, ROM and the like, and a display. The image processing program is installed in the ROM, and based on an instruction from a user the computer controls the display so as to display the medical information such as fundus images acquired from the server 140.

Figure 4:
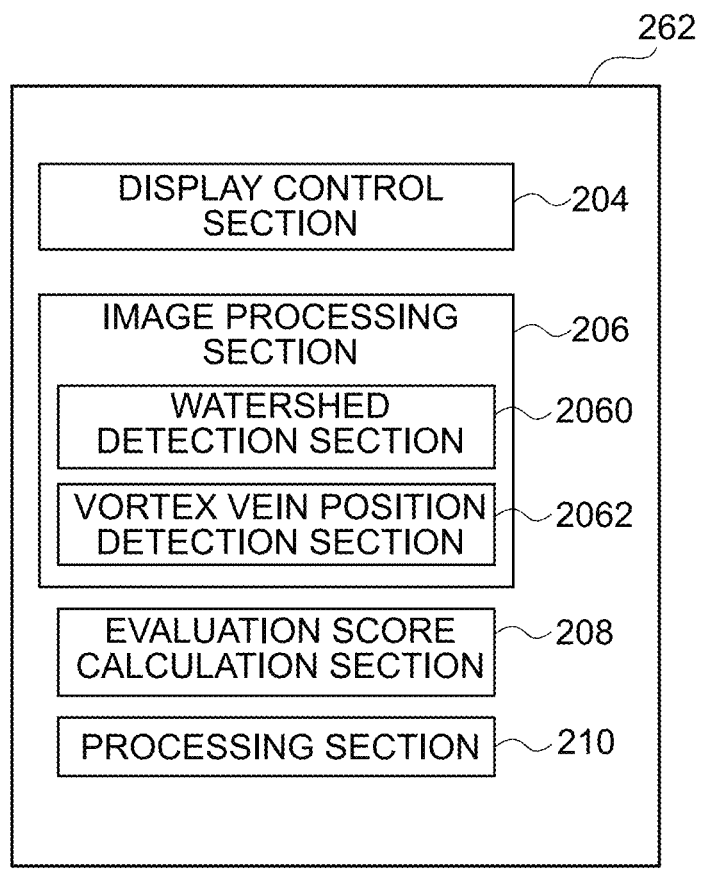
FIG. 4 is a block diagram illustrating functionality of a CPU 262 of a server 140.

Next, description follows regarding various functions implemented by the CPU 262 of the server 140 executing the image processing program, with reference to FIG. 4. The image processing program includes a display control function, an image processing function (watershed detection function, vortex vein position detection function), an evaluation score calculation function, and a processing function. By the CPU 262 executing the image processing program including each of these functions, the CPU 262 functions as a display control section 204, an image processing section 206 (watershed detection section 2060 and vortex vein position detection section 2062), an evaluation score calculation section 208, and a processing section 210, as illustrated in FIG. 4.

Figure 5:
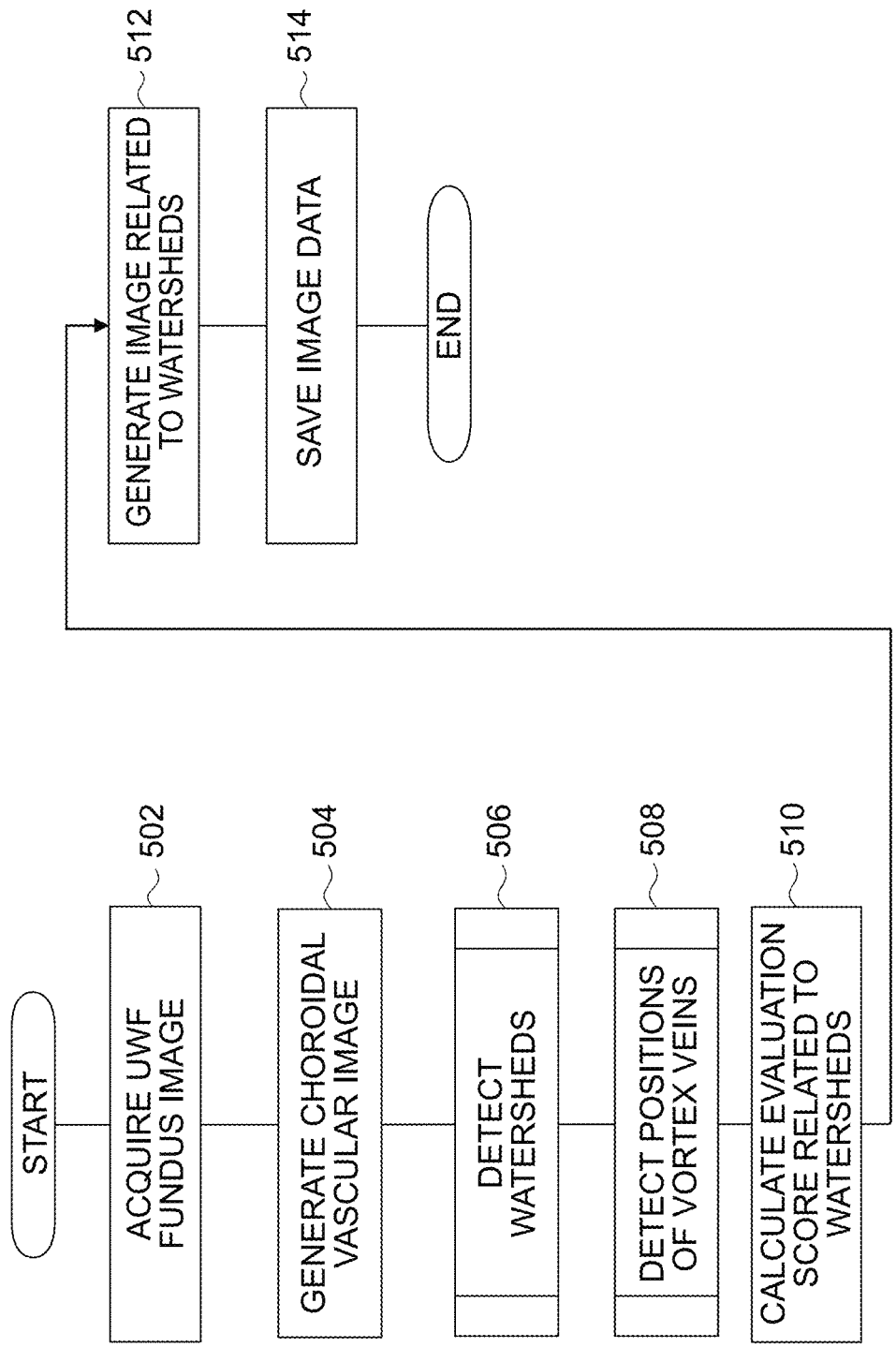
FIG. 5 is a flowchart of an image processing by the server 140.

Next detailed description follows regarding image processing by the server 140, with reference to FIG. 5. The image processing illustrated in the flowchart of FIG. 5 is implemented by the CPU 262 of the server 140 executing the image processing program. This image processing is started when a UWF fundus image (UWF-SLO image) is acquired by the ophthalmic device 110 and transmitted together with the patient ID to the server 140, and the server 140 has received the patient ID and the UWF fundus image.

Figure 11:
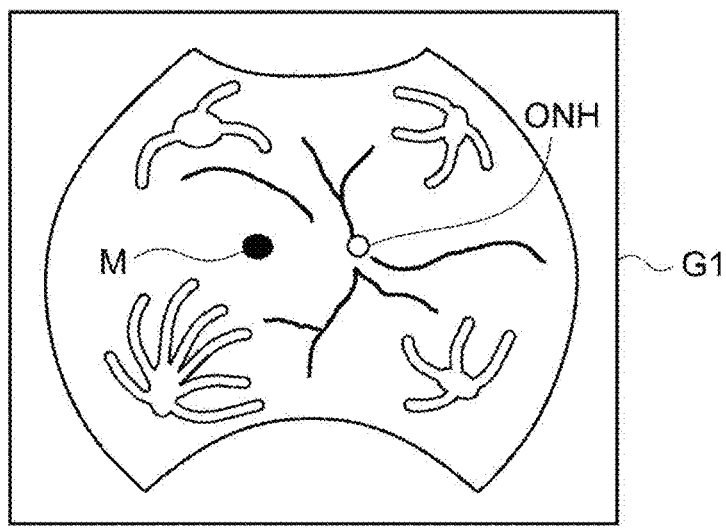
FIG. 11 is a diagram illustrating a RGB color fundus image G1.

At step 502, the processing section 210 acquires the UWF fundus image from the storage device 254. The UWF fundus image as described above encompasses a UWF-SLO image, and more specifically a blue fundus image, a green fundus image, a red fundus image, an IR fundus image, an RGB color fundus image, and an RG color fundus image. An RGB color fundus image G1 is illustrated in FIG. 11.

At step 504, the processing section 210 generates a choroidal vascular image in the following manner.

First explanation follows regarding information contained in the red fundus image and the green fundus image from out of UWF fundus images.

The structure of an eye is one in which a vitreous body is covered by plural layers of differing structure. The plural layers include, from the vitreous body at the extreme inside to the outside, the retina, the choroid, and the sclera. R light passes through the retina and reaches the choroid. The red fundus image therefore includes information relating to blood vessels present within the retina (retinal blood vessels) and information relating to blood vessels present within the choroid (choroidal blood vessels). In contrast thereto, G light only reaches as far as the retina. The green fundus image accordingly only includes information relating to the blood vessels present within the retina (retinal blood vessels).

Figure 12:
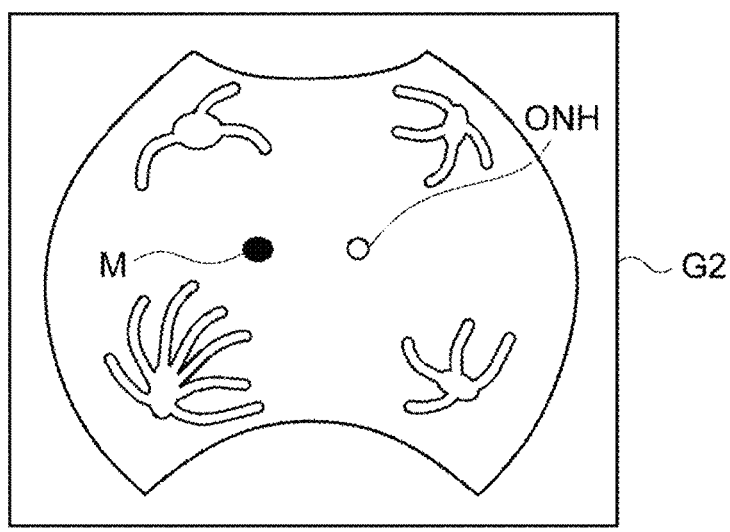
FIG. 12 is a diagram illustrating a choroidal vascular image G2.

The processing section 210 extracts the retinal blood vessels from the green fundus image by applying black hat filter processing to the green fundus image. Next, the processing section 210 removes the retinal blood vessels from the red fundus image by performing in-painting processing thereon using the retinal blood vessels extracted from the green fundus image. Namely, position information for the retinal blood vessels extracted from the green fundus image is employed when performing processing to infill the retinal blood vessel structure in the red fundus image using pixel values the same as those of surrounding pixels. The processing section 210 then emphasizes the choroidal blood vessels in the red fundus image by performing contrast limited adaptive histogram equalization (CLAHE) processing on the image data of the red fundus image from which the retinal blood vessels have been removed. The choroidal vascular image G2 illustrated in FIG. 12 was obtained in this manner. The generated choroidal vascular image is stored in the storage device 254.

The generation of the choroidal vascular image from the red fundus image and the green fundus image may be performed by the processing section 210 generating a choroidal vascular image using the red fundus image red fundus image or IR fundus image imaged with IR light.

A method to generate choroidal fundus images is disclosed in Japanese Patent Application No. 2018-052246 filed Mar. 20, 2018, the entirety of which is incorporated in the present specific by reference herein.

At step 506, the image processing section 206 detects watersheds of the choroidal vascular network in the choroidal vascular image G2.

Figure 6:
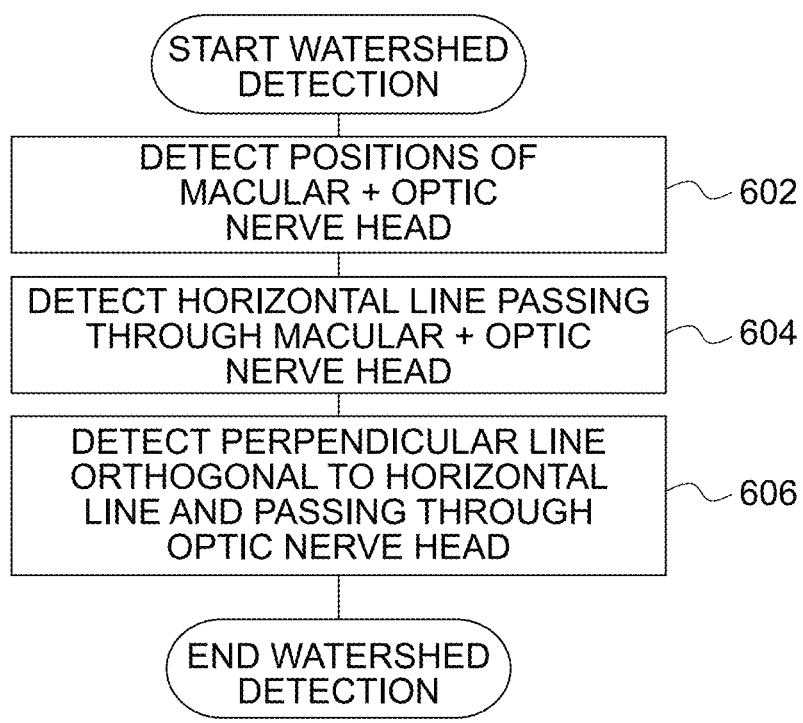
FIG. 6 is a flowchart of watershed detection processing (a first detection method) of step 506 of FIG. 5.

There are various methods employed as methods to detect watersheds in the technology disclosed herein. Firstly a first detection method for watersheds will be explained, with reference to FIG. 6.

A watershed is an area on the fundus with a lower density of choroidal blood vessels than other areas. Generally such areas where the density of choroidal blood vessels is lower than other areas are an area of a line connecting the position of the macula and the position of the optic nerve head, and an area of a straight line perpendicular to such a line passing through the position of the optic nerve head.

Note that in the present exemplary embodiment the line connecting the position of the macula and the position of the optic nerve head is a horizontal line.

In the present exemplary embodiment a watershed detection section 2060 detects such a horizontal line as a first watershed, and detects such a straight line as a second watershed. This is more specifically performed as follows.

Figure 13:
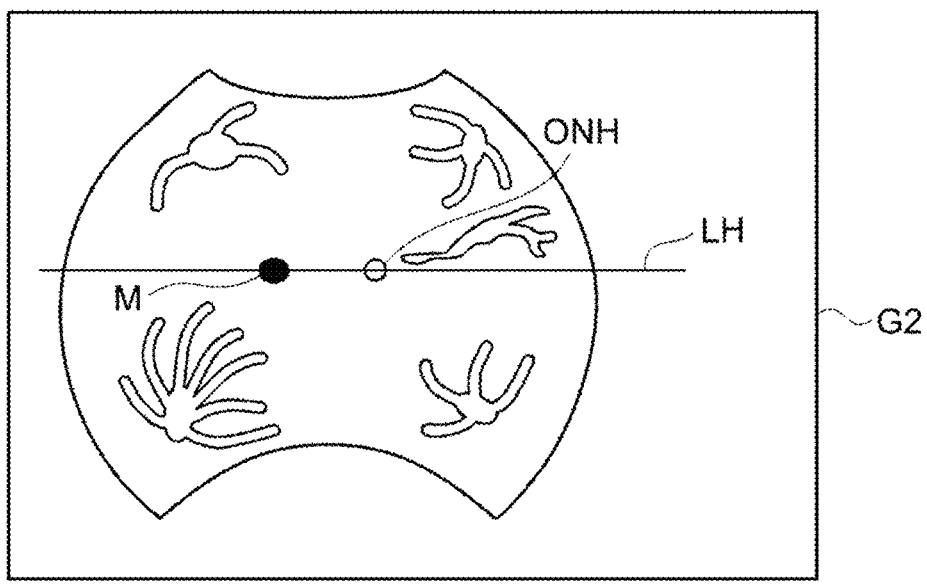
FIG. 13 is a diagram illustrating a manner by which respective positions of a macula M and an optic nerve head ONH are detected in the choroidal vascular image G2.

At step 602 the watershed detection section 2060 detects the respective positions of the macula M and the optic nerve head ONH in the choroidal vascular image G2, as illustrated in FIG. 13.

The macula is a dark area of the choroidal vascular image G2. The watershed detection section 2060 detects as the position of the macula M an area of a specific number of pixels having the smallest pixel value in the choroidal vascular image G2.

The watershed detection section 2060 detects a position of the optic nerve head ONH from the choroidal vascular image G2. More specifically, the watershed detection section 2060 detects the optic nerve head ONH in the choroidal vascular image G2 by performing pattern matching of a predetermined optic nerve head ONH image against the choroidal vascular image G2. Alternatively, the optic nerve head ONH is the brightest area of the choroidal vascular image G2, and so an area of a specific number of pixels having the greatest pixel value in the choroidal vascular image G2 may be detected as the position of the optic nerve head ONH.

Figure 14:
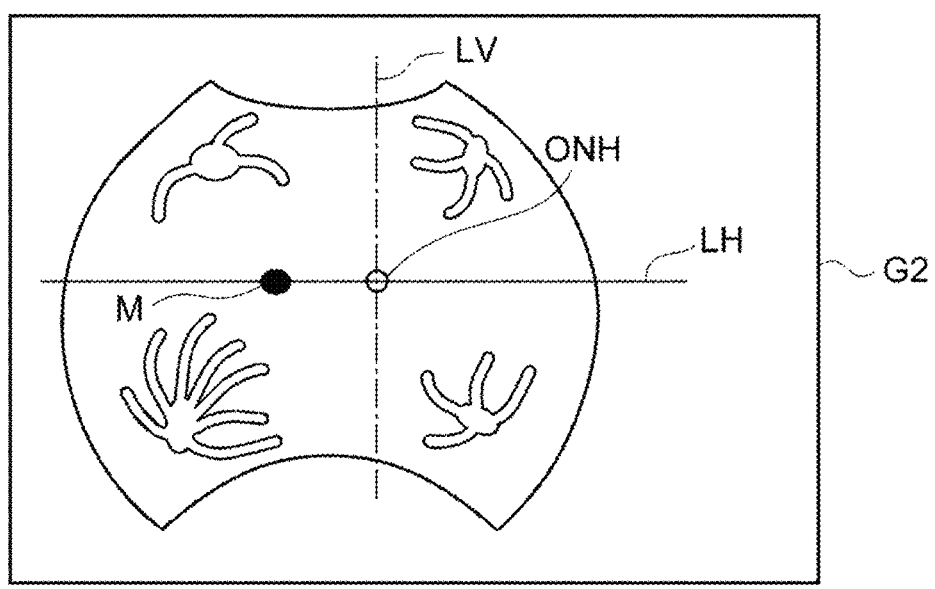
FIG. 14 is a diagram illustrating a manner by which a first watershed LH and a second watershed LV are detected.

At step 604 the watershed detection section 2060 detects, as a first watershed LH, a horizontal line connecting the position of the macula M and the position of the optic nerve head ONH together on the choroidal vascular image G2, as illustrated in FIG. 13. At step 606 the watershed detection section 2060 detects, as a second watershed LV, a straight line orthogonal to the horizontal line LH and passing through the position of the optic nerve head ONH, as illustrated in FIG. 14.

When the processing of step 606 has finished, the watershed detection processing of step 506 in FIG. 5 is ended, and the image processing transitions to step 508.

Figure 7:
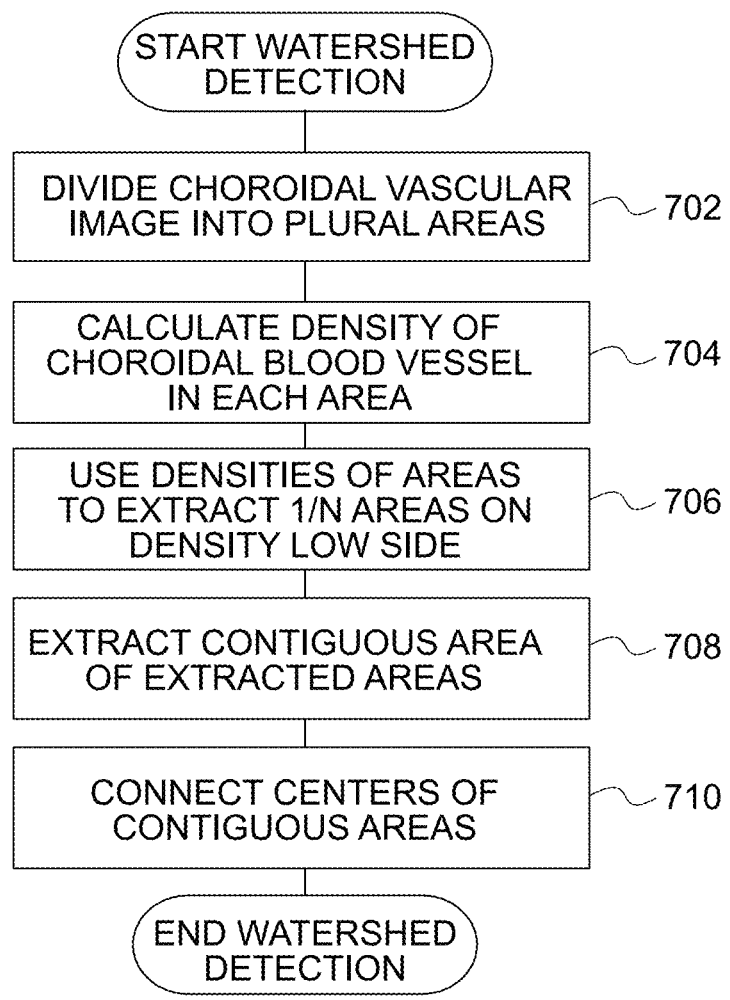
FIG. 7 is a flowchart of watershed detection processing (a second detection method) of step 506 of FIG. 5.

Explanation next follows regarding a second detection method for watersheds, with reference to FIG. 7.

As described above, a watershed is an area in the choroidal vascular image G2 having a lower density of choroidal blood vessels than other areas. In the second detection method the watershed detection section 2060 detects watersheds by connecting together centers of areas where the density is lower than other areas in the choroidal vascular image G2. This is more specifically performed as follows.

At step 702 the watershed detection section 2060 divides the choroidal vascular image G2 into plural areas that each include a specific fixed number of pixels.

At step 704 the watershed detection section 2060 calculates a density of choroidal blood vessels in each of the areas. More specifically, the watershed detection section 2060 first detects choroidal blood vessels in the choroidal vascular image G2 and calculates a density of choroidal blood vessels in each of the areas. Note that a choroidal blood vessel detection method is, for example, a method of extracting an area of the choroidal vascular image G2 including pixels having a higher pixel value (e.g. brightness value) than peripheral pixels as the choroidal blood vessels pixels.

At step 706, the watershed detection section 2060 takes the density of each of the respective areas, sorts the areas into sequence from the lowest density, and then extracts 1/n areas having a density on the lower side from the overall area (wherein n=100, for example).

At step 708 the watershed detection section 2060 extracts contiguous areas from the positions of each of the 1/n areas in the overall area.

Figure 15:
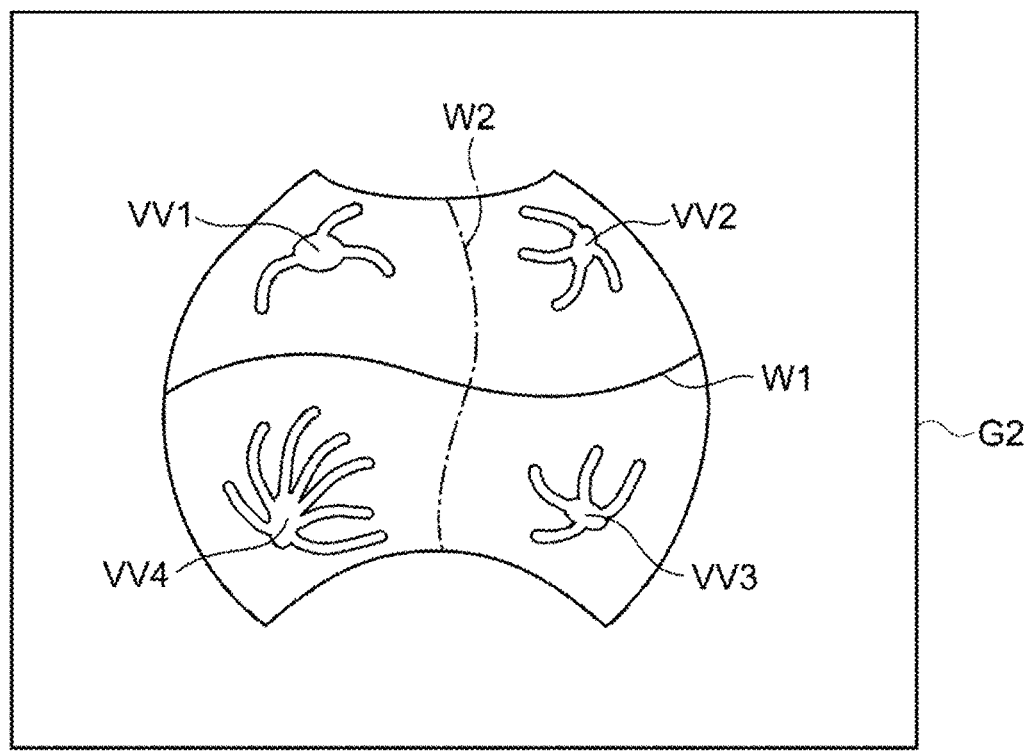
FIG. 15 is a diagram illustrating a manner by which watersheds W1, W2 are detected.

At step 710 the watershed detection section 2060 detects watersheds W1, W2 by connecting the centers of contiguous areas, as illustrated in FIG. 15.

When the processing of step 710 has finished, the watershed detection processing of step 506 of FIG. 5 is ended, and the image processing transitions to step 508.

Figure 8:
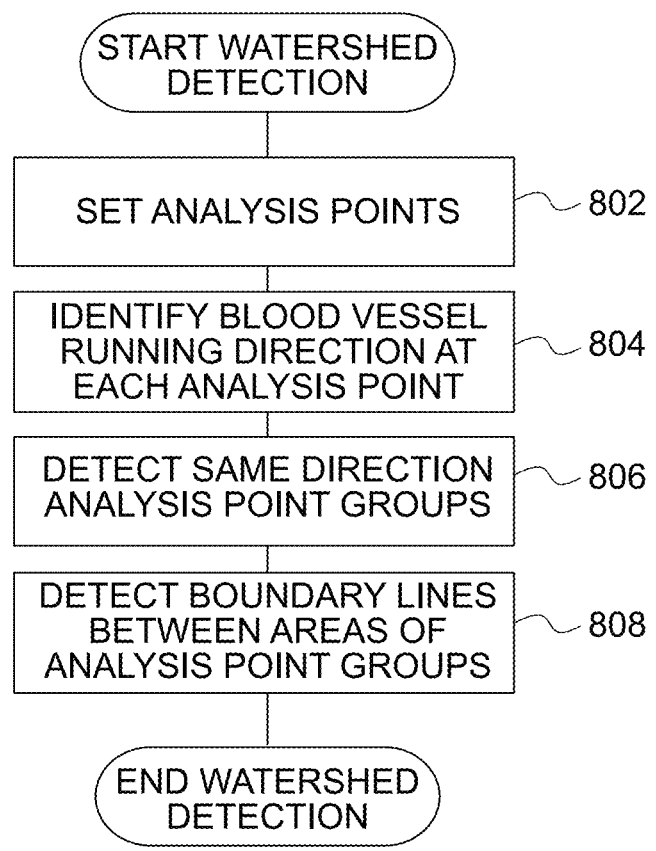
FIG. 8 is a flowchart of watershed detection processing (a third detection method) of step 506 of FIG. 5.

Next, description follows regarding a third detection method for watersheds, with reference to FIG. 8.

Figure 16:
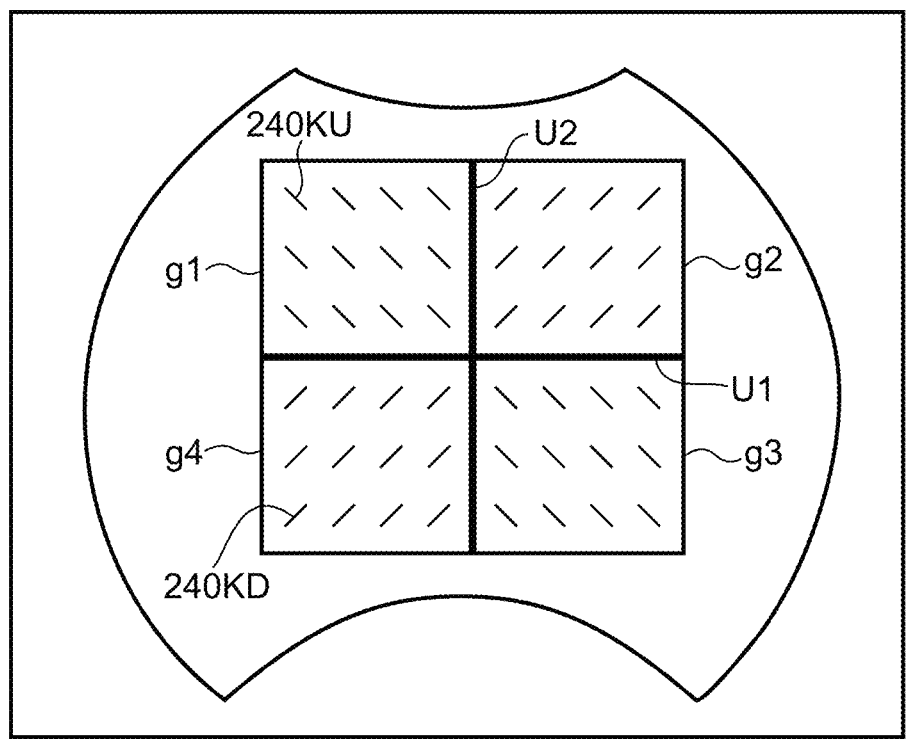
FIG. 16 is a diagram illustrating a manner by which areas are found from groups g1 to g4 of analysis point groups having the same blood vessel running direction, and watersheds are detected from boundaries to the areas.

As illustrated in FIG. 16, generally there are four vortex veins present on a fundus, with the choroidal blood vessels each connected to one of the four vortex veins, and in areas on the fundus where watersheds are thought to be present, the blood vessel running direction is the same direction for choroidal blood vessels connected to the same vortex vein. These watersheds are present at boundaries u1, u2 between areas of choroidal blood vessel groups from g1 to g4 connected to the same vortex vein.

In the third detection method, the watershed detection section 2060 extracts the choroidal vascular network from the choroidal vascular image, detects the running direction of each of the choroidal blood vessels in the choroidal vascular network, and detects watersheds from the running directions of each of the choroidal blood vessels. This is more specifically performed as follows.

At step 802, the watershed detection section 2060 sets plural analysis points in the choroidal vascular image G2. More specifically, the watershed detection section 2060 first detects the position of the macula and the optic nerve head as described above, and then uses a horizontal line connecting these positions to set a first area above the horizontal line in the choroidal vascular image G2 and a second area below the horizontal line. The watershed detection section 2060 arranges plural analysis points 240KU in the first area so as to be positioned at a uniform spacing from each other in a grid pattern having M (a natural number) rows arrayed along the vertical direction and N (a natural number) columns arrayed along the left-right (horizontal) direction. For example, the number of individual analysis points in the first area may be M (3)× N (7) (=L: 21). The watershed detection section 2060 arranges analysis points 240KD at positions in the second area so as to have line symmetry to the analysis points 240KU arranged in the first area with respect to the horizontal line.

Note that the analysis points 240KU, 240KD are not necessarily at a uniform spacing and are not necessarily in a grid pattern in the first area and the second area. The size of the first area and the second area may also be changed according to the eye axial length. The numbers L, M, and N may also be set to various values, and are not limited to the example described above. Resolution is improved by increasing the numbers.

At step 804 the watershed detection section 2060 identifies a movement direction of each of the choroidal blood vessels (blood vessel running direction) in the choroidal vascular image G2. More specifically, the watershed detection section 2060 executes the following processing on each of the analysis points 240KU, 240KD in the choroidal vascular image. Namely, for each of the analysis points 240KU, 240KD the watershed detection section 2060 sets an area (cell) having the respective analysis point 240KU, 240KD at the center, and creates a histogram of brightness gradient direction at each of the pixels in the cells. Next, the watershed detection section 2060 takes the gradient direction having the lowest count in the histogram of the cells as the movement direction for the pixels in each of the cells. This gradient direction corresponds to the blood vessel running direction. Note that the reason for taking the gradient direction having the lowest count as the blood vessel running direction is as follows. The brightness gradient is smallest in the blood vessel running direction, whereas the brightness gradient large in other directions (for example, there is a large difference in brightness between blood vessel and non-blood vessel tissue). Thus creating a histogram of brightness gradient for each of the pixels results in a smaller count in the blood vessel running direction. The blood vessel running direction at each of the analysis points 240KU, 240KD in the choroidal vascular image is identified by the processing described above.

At step 806 the watershed detection section 2060 detects a group of analysis points having the same direction. More specifically, the watershed detection section 2060 detects analysis points having the same direction as analysis point groups belonging to ranges of angle with respect to the horizontal line of the blood vessel running direction at each of the analysis points 240KU, 240KD, these ranges being, for example: from 0° up to but less than 90°, from 90° up to but less than 180°, from 180° up to but less than 270°, and from 270°) up to but less than 360°.

At step 808, the watershed detection section 2060 detects boundary lines between the analysis point group areas as watersheds. More specifically, the watershed detection section 2060 sets areas from g1 to g4 respectively containing analysis point groups belonging to the ranges in the choroidal vascular image G2 of: from 0° up to but less than 90°, from 90° up to but less than 180°, from 180° up to but less than 270°, and from 270° up to but less than 360°. The watershed detection section 2060 then detects boundary lines U1, U2 between the areas from g1 to g4 as watersheds.

When the processing of step 808 has finished the watershed detection processing of step 506 of FIG. 5 is ended, and the image processing transitions to step 508.

The watershed detection method is not limited to selection from the first detection method to the third detection method. The following detection methods are applicable in the technology disclosed herein.

For example, a method (fourth detection method) is to detect groups of pixels in the choroidal vascular image having local minima pixel values, and to connect areas having a higher frequency of local minima pixels than other areas.

Moreover, a method (fifth detection method) is to extract an area having a global minimum pixel values in the fundus image by subjecting the choroidal vascular image to low frequency processing.

Furthermore, a method (sixth detection method) is to take as watersheds areas of the pixels in the choroidal vascular image configured by pixels of lower values than a reference brightness. Note that the reference brightness in the sixth detection method is an average value of the choroidal vascular image pixel values.

At step 508 the vortex vein position detection section 2062 detects positions of vortex veins (hereafter referred to as VVs). The choroidal vascular image is analyzed and the vortex vein positions detected. Choroidal blood vessel information indicating a network and structure of the choroidal blood vessels, such as the running direction of the choroidal blood vessels, the blood vessel diameter (thickness of blood vessels), the surface area of blood vessels, branching/merging of the blood vessels, and the like may be employed when performing this analysis. For example, the positions of the vortex veins may be detected by a combination of the blood vessel running direction and the blood vessels thickness and the branch points/merge points of the blood vessels.

Figure 9:
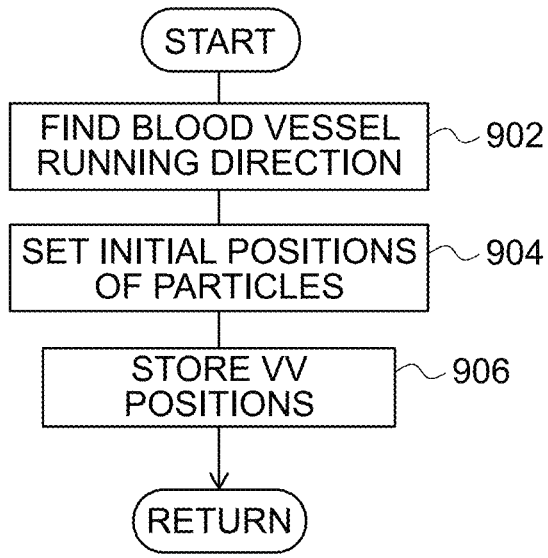
FIG. 9 is a flowchart of first vortex vein position detection processing of processing for detection of the position of a vortex vein of step 508 of FIG. 5.
Figure 10:
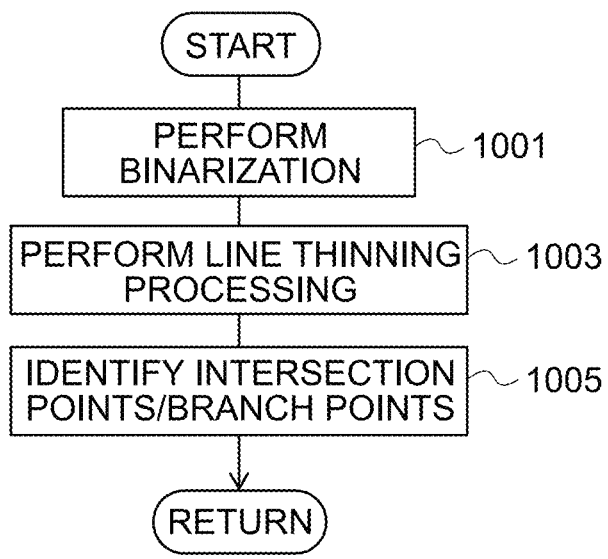
FIG. 10 is a flowchart of second vortex vein position detection processing of processing for detection of the position of a vortex vein of step 508 of FIG. 5.

Explanation follows regarding a specific method of vortex vein position detection processing of step 508, with reference to FIG. 9 and FIG. 10.

FIG. 9 illustrates a flowchart of first vortex vein position detection processing and FIG. 10 illustrates a flowchart of second vortex vein position detection processing. Either the first vortex vein position detection processing (FIG. 9) or the second vortex vein position detection processing (FIG. 10) may be employed as the vortex vein position detection processing. Moreover, the vortex vein positions may be detected by taking a product of the results of the first vortex vein position detection processing (FIG. 9) and the second vortex vein position detection processing (FIG. 10) (taking as vortex vein positions only positions detected by both the processing of FIG. 9 and by the processing of FIG. 10).

First explanation follows regarding first vortex vein position detection processing of FIG. 9.

At step 902 the vortex vein position detection section 2062 finds the blood vessel running direction. The processing of step 902 is the same as the processing of steps 802, 804 of FIG. 8 and so explanation thereof will be omitted.

At step 904 the vortex vein position detection section 2062 sets initial positions of particles at one or other of the above analysis points.

At step 906 the vortex vein position detection section 2062 acquires the blood vessel running direction at each of the initial positions. Each of the hypothetical particles is then moved by a specific distance along the acquired blood vessel running direction, and then the blood vessel running direction re-acquired at the moved-to position, before the hypothetical particle is again moved by the specific distance along the acquired blood vessel running direction. This operation of moving by the specific distance along the blood vessel running direction is repeated for a pre-set number of movements.

This processing is executed at the positions of all of the analysis points. At the point in time when a set number of movements have been performed on all of the hypothetical particles, any points where a fixed number of the hypothetical particles have congregated are then taken as VV positions and stored in the storage device 254.

Next, description follows regarding the second vortex vein position detection processing of FIG. 10.

At step 1001 the vortex vein position detection section 2062 creates a binarized image by performing binarization of the choroidal vascular image using a specific threshold.

At step 1003 the vortex vein position detection section 2062 performs fine line processing on the binarized image so as to convert into a line image having a width of 1 pixel and to discard the thickness information.

At step 1005 the vortex vein position detection section 2062 identifies blood vessel characteristic points including characteristic patterns in the line image, such as blood vessel intersection points where lines intersect and blood vessel branch points where lines branch, as VVs. The blood vessel characteristic points are stored in the storage device 254 as VV positions.

The vortex vein position detection processing of step 508 of FIG. 5 is thereby finished, and the image processing proceeds to step 510.

At step 510 the evaluation score calculation section 208 calculates evaluation scores related to the watersheds. There are various evaluation scores employable as the evaluation scores related to the watersheds, such as an evaluation score of the watershed itself or an evaluation score determined by a relationship between the watershed and a structure of the fundus (a vortex vein, for example). More specifically there are the following evaluation scores.

First Evaluation Score

Figure 17:
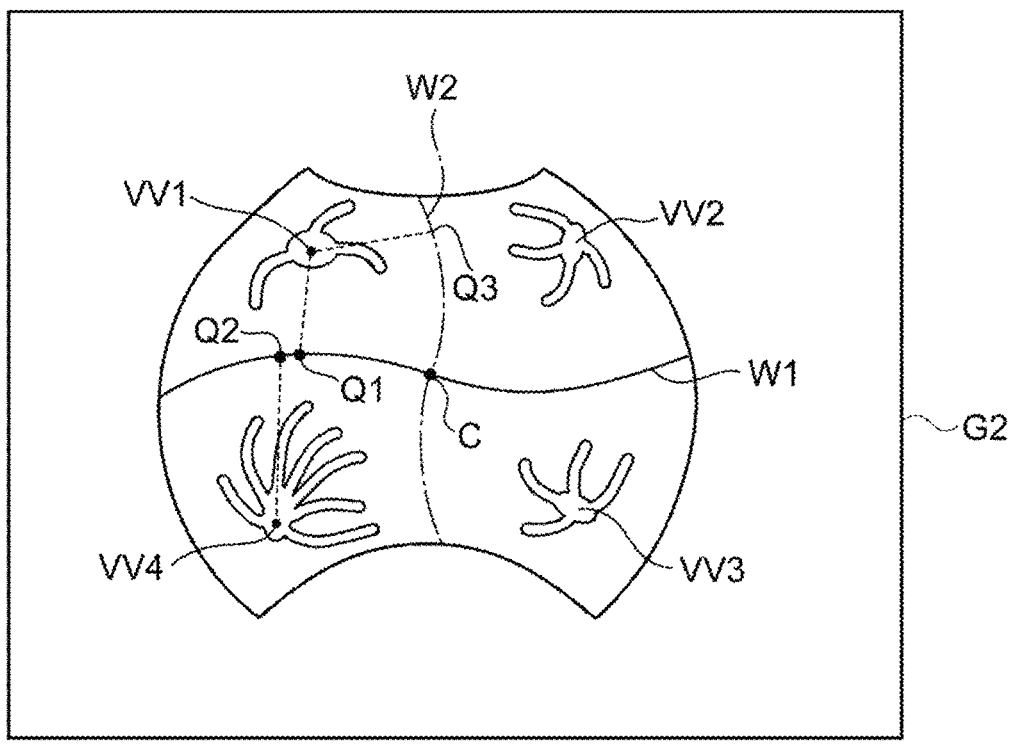
FIG. 17 is a diagram illustrating content of a first evaluation value.

First explanation follows regarding a first evaluation score for watersheds. The first evaluation score is a distance between a vortex vein and a watershed, and more specifically is, as illustrated in FIG. 17, distances between each of the vortex veins VV1 to VV4 and a first watershed W1 and a second watershed W2. These distances are, for example, the following three types of distance.

First: a length of a perpendicular line from each of the vortex veins VV1 to VV4 to the first watershed W1. More specifically for example, as illustrated in FIG. 17, the evaluation score calculation section 208 calculates the distance of each point on the first watershed W1 to the vortex vein VV1, detects point Q1 having the smallest distance, and stores the distance between the vortex vein VV1 and the point Q1 as the perpendicular line length to the first watershed W1 in the storage device 254.

Second: a perpendicular line length to the second watershed W2 from each of the vortex veins VV1 to VV4. Similarly to with the perpendicular line length to the first watershed W1 the evaluation score calculation section 208 calculates, for example, the distance of each of the points of the second watershed W2 to the vortex vein VV1, detects a point Q3 having the smallest distance, and stores the distance between the vortex vein VV1 and the point Q3 as the perpendicular line length to the second watershed W2 in the storage device 254.

Third: a distance from each of the vortex veins VV1 to VV4 to an intersection point C between the first watershed W1 and the second watershed W2.

Second Evaluation Score

Explanation follows regarding the second evaluation score for watersheds. The second evaluation score is a value indicating a degree of symmetry of vortex veins with respect to the watersheds. More specifically, the evaluation score calculation section 208 calculates the following value RV indicating the degree of symmetry for each pair of pairs of vortex veins positioned at positions facing each other across the first watershed W1 (for example, vortex veins VV1, VV4).

For example: a value RV1 indicating a degree of symmetry of the vortex vein VV1 with respect to the vortex vein VV4 is RV1=(distance between VV1 and Q1)/(distance between VV4 and Q2); a value RV4 indicating the degree of symmetry of the vortex vein VV4 with respect to the vortex vein VV1 is RV4=(distance between VV4 and Q2)/(distance between VV1 and Q1).

The closer the degree of symmetry values (RV1, RV2) are to 1, the higher the degree of symmetry for the pairs of vortex veins positioned at positions facing each other across the first watershed W1.

Third Evaluation Score

Next, description follows regarding the third evaluation score for watersheds. The third evaluation score is a value indicating a degree of asymmetry of choroidal blood vessels with respect to the watersheds. The evaluation score calculation section 208 employs, for example, a least squares method to find a straight line for the first watershed W1, and takes the straight line found thereby to define a new reference line.

In the example described above (step 802 of FIG. 8), the first area and the second area are set with respect to the horizontal line connecting the position of the macula M and the position of the optic nerve head ONH.

To find the third evaluation score, the evaluation score calculation section 208 sets, with reference to the new reference line, a first area as an area above the new reference line and s second area as below the new reference line, and then sets analysis points in the first area and the second area so as to have line symmetry to each other with respect to the new reference line.

The evaluation score calculation section 208 identifies the blood vessel running direction at each of the analysis points.

The evaluation score calculation section 208 computes a value indicating a degree of asymmetry for each analysis point pair having line symmetry about the new reference line. The value indicating the degree of asymmetry is a difference in the blood vessel running directions, and this difference is derived from histograms of the respective analysis point pairs. The evaluation score calculation section 208 finds a number of degrees difference $\Delta h$ for each bin of histogram pairs, and then takes the square of $\Delta h$. The value indicating the degree of asymmetry is found by calculating $\Sigma \Delta h^2$, which is the sum of $\Delta h^2$ for each of the bins. The larger $\Sigma \Delta h^2$ is the larger the difference in the shape of the histograms and the larger the degree of asymmetry, and the smaller $\Sigma\Delta h^2$ is the more similar the shapes of the histograms and the smaller the degree of asymmetry.

Note that the value indicating the degree of asymmetry is not limited to this sum of the squares of errors in the histograms for the analysis point pairs. A representative angle may be determined from the histograms of the analysis points in each of the respective pairs, and a difference in the absolute values thereof computed.

Fourth Evaluation Score

Figure 18:
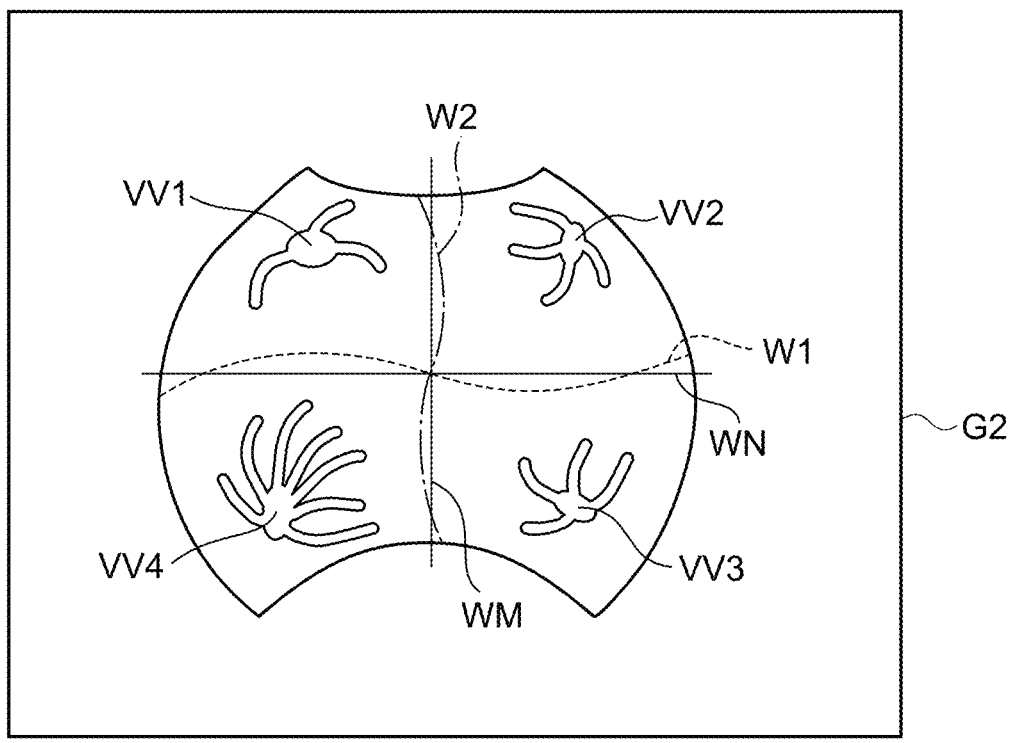
FIG. 18 is a diagram illustrating a first watershed axis WN and a second watershed axis WM.

Next, description follows regarding the fourth evaluation score for watersheds. The fourth evaluation score is an angle formed between watersheds. The evaluation score calculation section 208 employs a least squares method to find straight lines for each of the first watershed W1 and the second watershed W2, and to thereby find a first watershed axis WN and a second watershed axis WM, as illustrated in FIG. 18.

Figure 19:
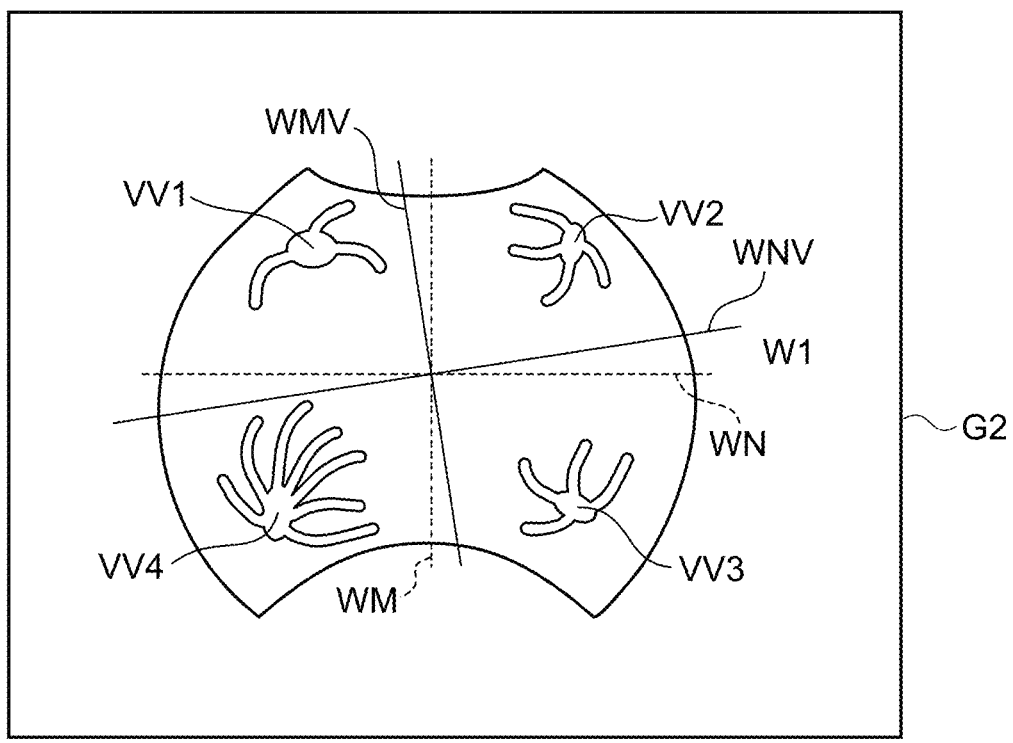
FIG. 19 is a diagram illustrating a new first watershed axis WNV and a new second watershed axis WMV.

From the first watershed axis WN and the second watershed axis WM, the evaluation score calculation section 208 then generates a new first watershed axis WNV and a new second watershed axis WMV that are orthogonal to each other, as illustrated in FIG. 19.

Figure 20:
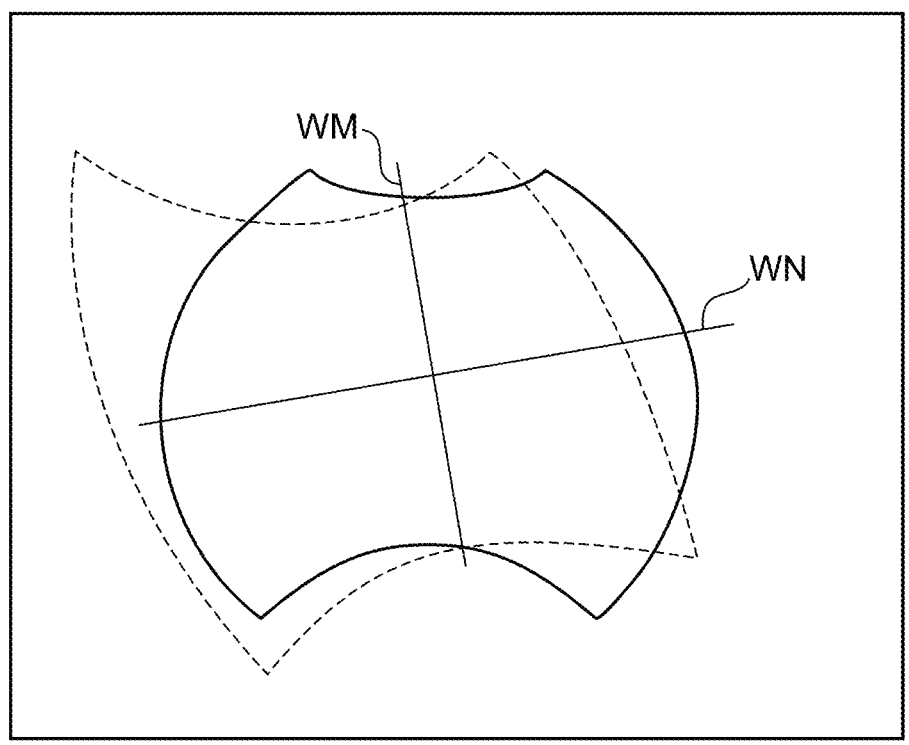
FIG. 20 is a diagram illustrating a manner by which a choroidal vascular image is affine transformed to match the new first watershed axis WNV and the new second watershed axis WMV.

As illustrated in FIG. 20, the evaluation score calculation section 208 affine transforms the choroidal vascular image as defined by the first watershed axis WN and the second watershed axis WM so as to match the new first watershed axis WNV and the new second watershed axis WMV.

The evaluation score calculation section 208 then derives the first evaluation score to the third evaluation score as described above with respect to the affine transformed choroidal vascular image as the fourth evaluation score (No. 1 fourth evaluation score).

The fourth evaluation score is not limited thereto.

For example, the evaluation score calculation section 208 may be configured so as find the first evaluation score to the third evaluation score as described above while using the first watershed axis WN and the second watershed axis WM illustrated in FIG. 18 on the choroidal vascular image prior to affine transformation as the first watershed W1 and the second watershed W2, as the fourth evaluation score (No. 2 fourth evaluation score). Furthermore, the evaluation score calculation section 208 may also find the first watershed axis WN and the second watershed axis WM and the new first watershed axis WNV and the new second watershed axis WMV not on a two dimensional choroidal vascular image, but on a great circle (of an eyeball model). The evaluation score calculation section 208 may also find the first evaluation score to the third evaluation score, the No. 1 fourth evaluation score, and the No. 2 fourth evaluation score based on the first watershed axis WN and the second watershed axis WM and on the new first watershed axis WNV and the new second watershed axis WMV as defined on a great circle, as the fourth evaluation score (No. 3 fourth evaluation score).

Fifth Evaluation Score

Next, description follows regarding a fifth evaluation score for watersheds. At the first watershed W1 and the second watershed W2 there is a low density of choroidal blood vessels as described above, however there is variation in the brightness values of the pixels in the choroidal vascular image. The evaluation score calculation section 208 finds an average value of the brightness values for all of the pixels in the first watershed W1 and the second watershed W2. The evaluation score calculation section 208 finds, as the fifth evaluation score, a difference between the brightness values of pixels in a pathological lesion or the vortex vein portions, of a fundus pre-stored in the storage device 254, and the average value.

Sixth Evaluation Score

Figure 21:
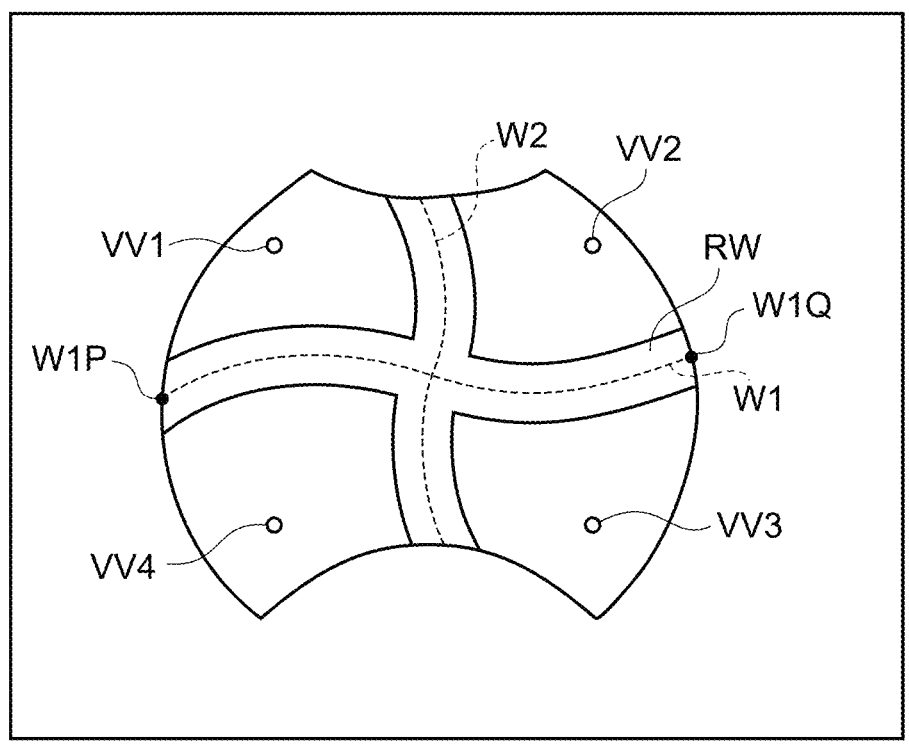
FIG. 21 is a diagram illustrating a watershed area RW.

Next, description follows regarding a sixth evaluation score for watersheds. As in the sixth detection method, when an area RW (see FIG. 21) configured from pixels having lower values than a reference brightness for each of the pixels in the choroidal vascular image is found as watersheds, a surface area of the area RW is employed as the sixth evaluation score.

Seventh Evaluation Score

Next, description follows regarding a seventh evaluation score for watersheds. The seventh evaluation score is a value indicating the tortuosity of each of the watersheds themselves. This is more specifically as follows.

The evaluation score calculation section 208 finds the first watershed axis WN and the second watershed axis WM by finding straight lines for each of the first watershed W1 and the second watershed W2 as described above (see FIG. 18), and then finds the respective lengths DWN, DWM of the first watershed axis WN and the second watershed axis WM.

The evaluation score calculation section 208 also finds the respective lengths DW1, DW2 of the first watershed axis WN and the second watershed axis WM.

The evaluation score calculation section 208 then takes the following values as the value indicating the tortuosity of each of the first watershed W1 and the second watershed W2 to find the seventh evaluation score.

(DW1/DWN)−1

(DW2/DWM)−1

Note that DW1, DWN, DW2, DWM may be distances on a two dimensional choroidal vascular image, or may be distances on a three-dimensional eyeball model.

Eighth Evaluation Score

Next, description follows regarding the eighth evaluation score for watersheds. The eighth evaluation score is the surface area of choroidal blood vessels present in areas resulting from subdividing the choroidal vascular image using the watersheds. The evaluation score calculation section 208 sub-divides the choroidal vascular image into plural areas with respect to the watersheds, and computes as the eighth evaluation score the surface area of choroidal blood vessels present in each of the plural sub-divided areas. This is more specifically performed as follows.

First, more specifically, these are respectively the surface areas of the choroidal blood vessels connected to the same vortex vein present in each of four areas resulting from sub-dividing the choroidal vascular image using the first watershed W1 and the second watershed W2.

The evaluation score calculation section 208 sub-divides the choroidal vascular image with respect to the first watershed W1 and the second watershed W2. The evaluation score calculation section 208 extracts the choroidal blood vessels connected to the same vortex vein present in each of the four sub-divided areas. The evaluation score calculation section 208 finds the surface area of the extracted choroidal blood vessels respectively connected to the same vortex vein present in each of the four areas, and employs this as the eighth evaluation score.

Second, the surface area of choroidal blood vessels present in each of two areas resulting from sub-dividing the choroidal vascular image with respect to the first watershed W1 or the second watershed W2. Note that the two sub-divided areas with respect to the first watershed W1 are an area on the upper side of the first watershed W1 (above the ear) and an area on the lower side of the first watershed W1 (below the ear).

When the evaluation score has been calculated as described above, the processing of step 510 finishes, and the image processing proceeds to step 512.

At step 512 the processing section 210 generates data for a screen related to watersheds, and at step 514 the processing section 210 saves (stores) the screen data in the storage device 254.

The processing section 210 transmits the screen data to the viewer 150. The viewer 150 displays the screen on a display. The display control section 204 of the server 140 may display the screen related to watersheds on the display 256.

Next, description follows regarding a first fundus image display screen 1000A and a second fundus image display screen 1000B related to watersheds, with reference to FIG. 22 to FIG. 25.

Figure 22:
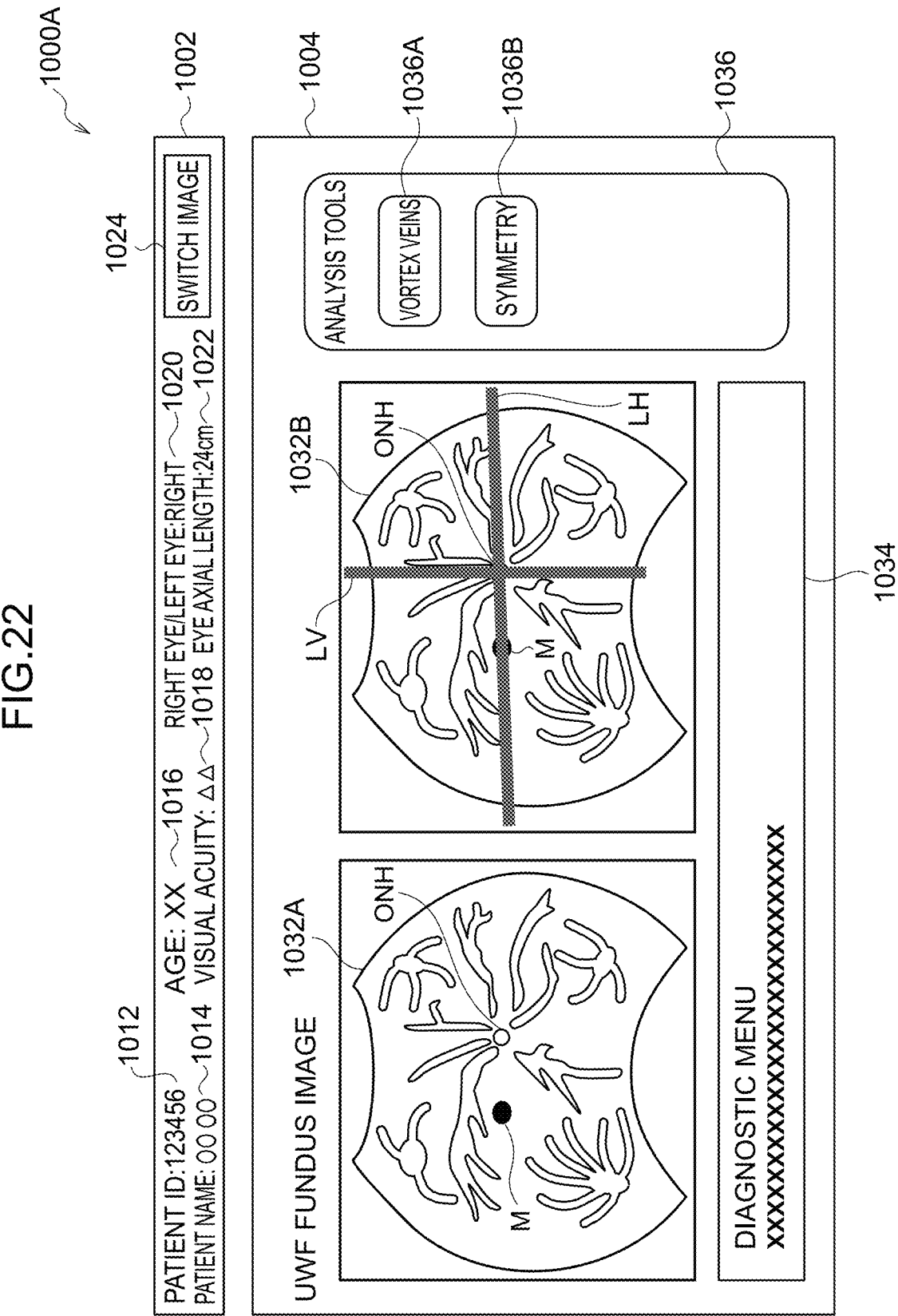
FIG. 22 is a diagram illustrating a first fundus image display screen 1000A including an image of watersheds LH, LV detected by the first detection method displayed overlaid on a UWF fundus image.

As illustrated in FIG. 22, the first fundus image display screen 1000A includes a patient information display field 1002 and a first fundus image information display field 1004A.

The patient information display field 1002 is for displaying the patient ID, the patient name, the patient age, the visual acuity of the patient, left eye/right eye information, and eye axial length, and includes display fields from 1012 to 1022, and a screen switch button 1024. The received patient ID, patient name, patient age, patient visual acuity, left eye/right eye information, and eye axial length are displayed in the display fields from 1012 to 1022.

The first fundus image information display field 1004A includes a UWF fundus image display field 1032A, a watershed image display field 1032B, an analysis tool display field 1036, and an information display field 1034.

A UWF fundus image (original fundus image), for example a RGB color fundus image (see FIG. 11) is displayed in the UWF fundus image display field 1032A.

An image of watersheds overlaid on the original fundus image is displayed in the watershed image display field 1032B. The watersheds for overlaid display are watersheds obtained by any one of the first detection method to the sixth detection method. Note that in FIG. 22 the overlaid watersheds LH, LV are those detected by the first detection method. Note that in the watershed image display field 1032B an overlaid image of watersheds may be displayed on a choroidal vascular image instead of on the original fundus image.

Comments and memos during examination by a user (ophthalmologist) are displayed as text in the information display field 1034.

In the analysis tool display field 1036A there is a vortex vein display instruction icon 1036A displayed to instruct overlaid display of the vortex veins in the UWF fundus image display field 1032A and in the watershed image display field 1032B. A symmetry display instruction icon 1036B is displayed in the analysis tool display field 1036 to instruct overlaid display of values indicating degree of symmetry in the watershed image display field 1032B.

Figure 23:
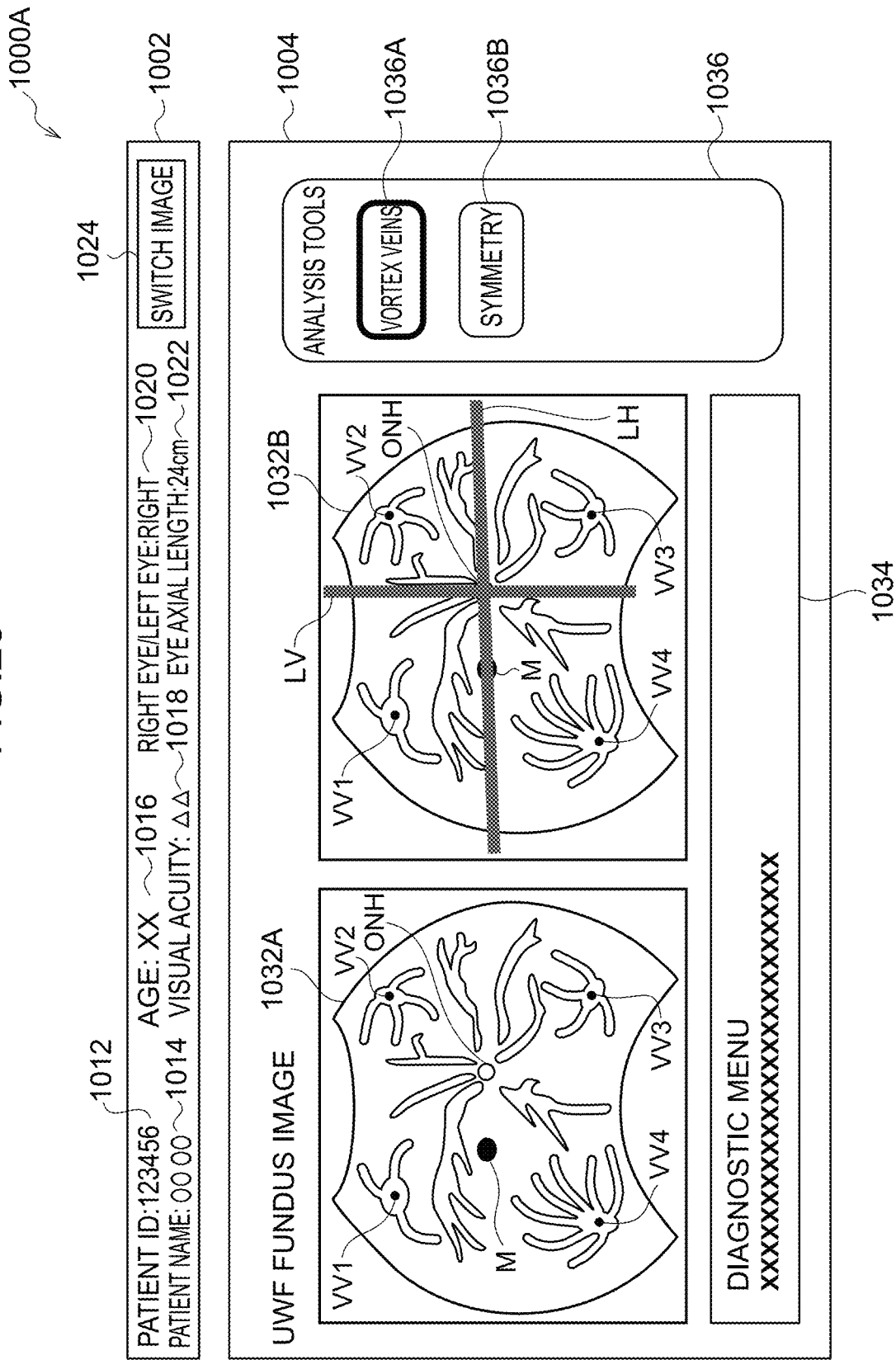
FIG. 23 is a diagram illustrating a first fundus image display screen 1000A including a UWF fundus image, and an image of vortex veins displayed overlaid on an image in which watersheds LH, LV have been displayed overlaid on the UWF fundus image.

In cases in which the vortex vein display instruction icon 1036A has been operated, the viewer 150 displays the vortex veins VV1 to VV4 so as to be respectively overlaid on the UWF fundus image display field 1032A and the watershed image display field 1032B in the first fundus image display screen 1000A, as illustrated in FIG. 23.

Figure 24:
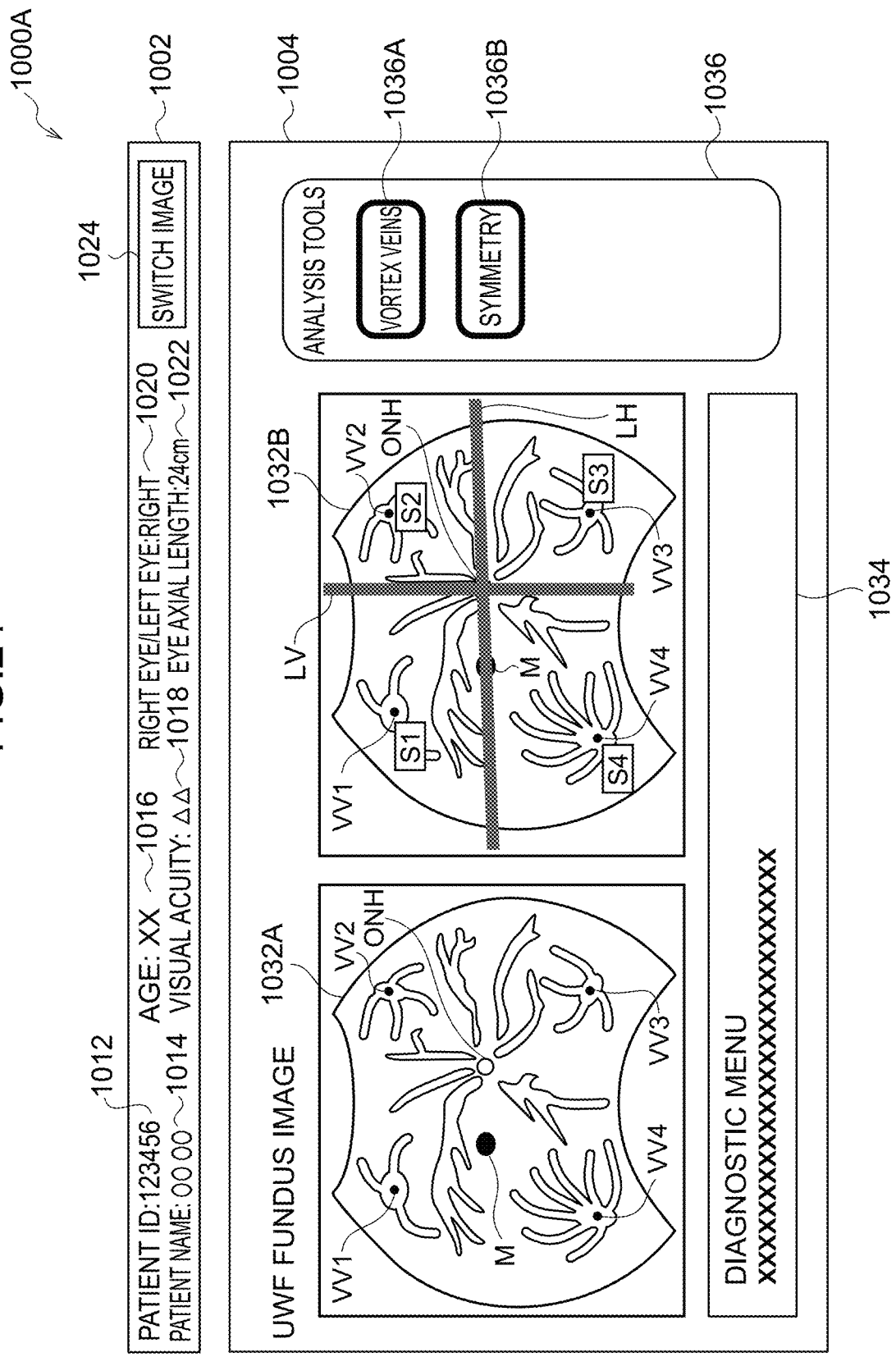
FIG. 24 is a diagram illustrating a first fundus image display screen 1000A including an image of vortex veins further displayed overlaid on the display content of FIG. 23.

In cases in which the symmetry display instruction icon 1036B has been operated, the viewer 150 displays values indicating the degree of symmetry overlaid on the watershed image display field 1032B in the first fundus image display screen 1000A, as illustrated in FIG. 24. In the example illustrated in FIG. 24, the values S1 to S4 indicate the degree of symmetry, namely are values RV1, RV2 that are the second evaluation scores or the like.

The analysis tool display field 1036 is not limited to the symmetry display instruction icon 1036B, and an icon may be included to instruct display of evaluation scores other than the second evaluation scores, such that when this icon is operated evaluation scores are displayed corresponding to the operated icon.

Figure 25:
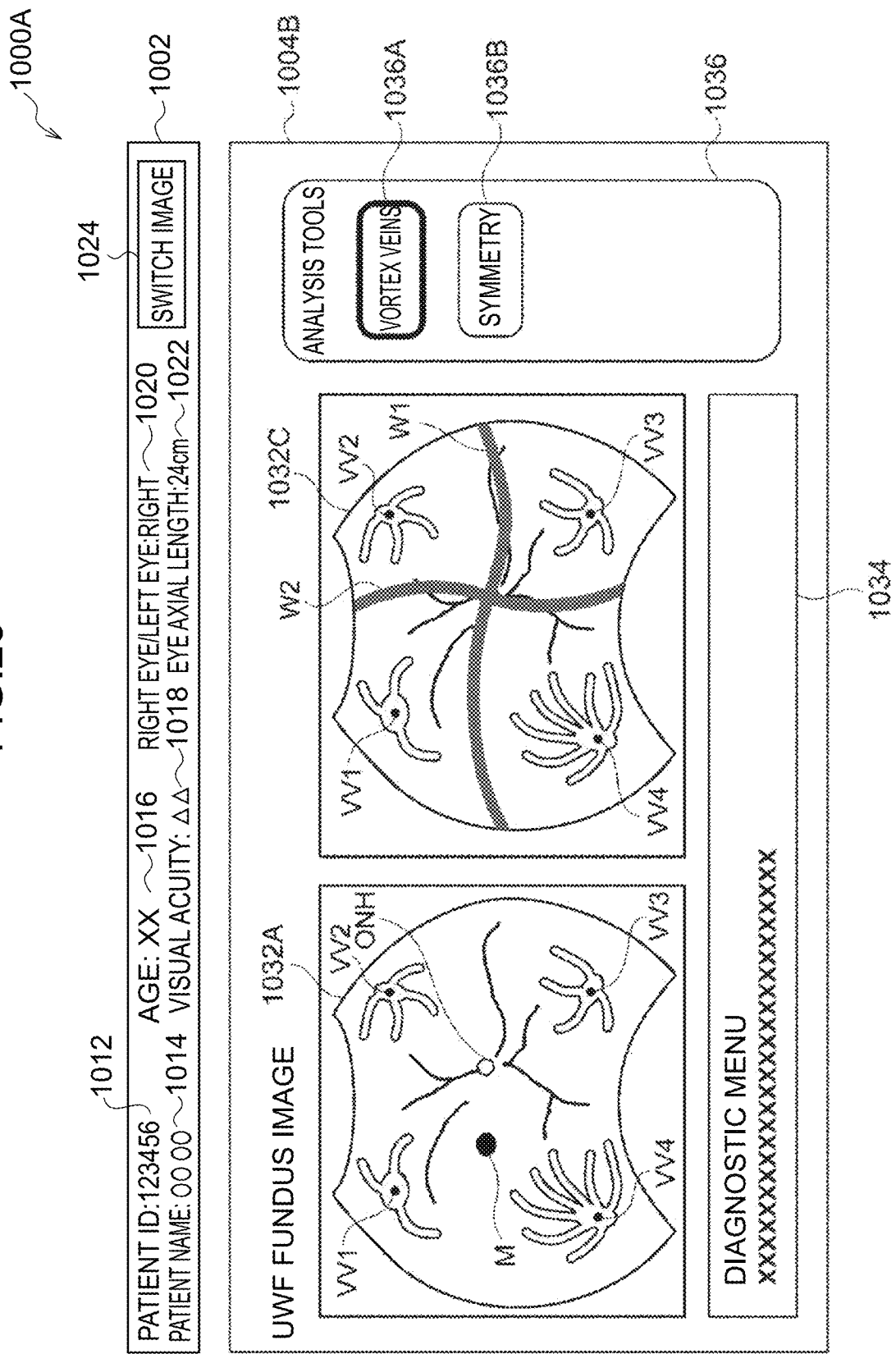
FIG. 25 is a diagram illustrating a second fundus image display screen 1000B.

When the screen switch button 1024 is operated on the first fundus image display screen 1000A, the viewer 150 displays the second fundus image display screen 1000B illustrated in FIG. 25 on the display.

The first fundus image display screen 1000A and the second fundus image display screen 1000B have substantially similar content, and the same reference numerals are appended to similar parts and explanation thereof will be omitted, with explanation only of the differing parts.

The second fundus image display screen 1000B includes a watershed image display field 1032C instead of the watershed image display field 1032B. The watersheds detected by a detection method different to the first detection method are displayed overlaid on the watershed image display field 1032C. The watersheds W1, W2 illustrated in FIG. 15 are displayed overlaid in FIG. 25.

As described above, in the above exemplary embodiments the watersheds of the choroidal vascular network are detected in the choroidal vascular image, thereby enabling a state of the choroidal blood vessels to be detected.

In the exemplary embodiments described above, in cases in which watersheds are detected from a horizontal line passing through the position of the optic nerve head and the position of the macula and from a straight line orthogonal to the horizontal line and passing through the optic nerve head, watershed detection can be performed simply by using the watershed detection processing to detect watersheds found from the density of choroidal blood vessels.

In the exemplary embodiments described above, the watersheds can be detected accurately by detecting watersheds through the detection of areas of lower density of choroidal blood vessels in the choroidal vascular image than other areas, and by detecting watersheds from the horizontal line and the straight line passing through the optic nerve head.

In the exemplary embodiments described above the watersheds are displayed, and so the state of the choroidal blood vessels can be made known to an ophthalmologist or the like.

In the example described above, the image processing of FIG. 5 is executed by the server 140, however the technology disclosed herein is not limited thereto. For example, this processing may be executed by the ophthalmic device 110 or the viewer 150, or a separate other image processing device may be connected to the network 130 and this processing executed by this image processing device.

Although explanation has been given in the exemplary embodiments described above regarding an example in which a computer is employed to implement image processing using a software configuration, the technology disclosed herein is not limited thereto. For example, instead of a software configuration employing a computer, the image processing may be executed solely by a hardware configuration such as a field programmable gate array (FPGA) or an application specific integrated circuit (ASIC). Alternatively, a configuration may be adopted in which some processing out of the image processing is executed by a software configuration, and the remaining processing is executed by a hardware configuration.

Such technology disclosed herein encompasses cases in which the image processing is implemented by a software configuration utilizing a computer, and also image processing implemented by a configuration that is not a software configuration utilizing a computer, and encompasses the following first technology to third technology.

First Technology

An image processing device including an acquisition section that acquires a fundus image, a generation section that generates a choroidal vascular image from the fundus image, and a detection section that detects a watershed of a choroidal vascular network in the choroidal vascular image.

Note that the processing section 210 of the exemplary embodiment described above is an example of the "acquisition section" and the "generation section" of the above first technology, and the watershed detection section 2060 of the exemplary embodiment described above is an example of the "detection section" of the above first technology.

The following second technology is proposed from the content disclosed above.

Second Technology

An image processing method including acquiring a fundus image using an acquisition section, generating a choroidal vascular image from the fundus image using a generation section, and detecting a watershed of a choroidal vascular network in the choroidal vascular image using a detection section.

The following third technology is proposed from the content disclosed above.

Third Technology

A computer program product for image processing in which the computer program product includes a computer-readable storage medium that is not itself a transient signal, wherein a program is stored on the computer-readable storage medium. The program causing a computer to execute processing including acquiring a fundus image, generating a choroidal vascular image from the fundus image, and detecting a watershed of a choroidal vascular network in the choroidal vascular image.

It must be understood that the image processing described above is merely an example thereof. Obviously redundant steps may be omitted, new steps may be added, and the processing sequence may be swapped around within a range not departing from the spirit of technology disclosed herein.

All publications, patent applications and technical standards mentioned in the present specification are incorporated by reference in the present specification to the same extent as if each individual publication, patent application, or technical standard was specifically and individually indicated to be incorporated by reference.

The invention claimed is:

1. An image processing method comprising:
   a processor acquiring a fundus image;
   the processor generating a choroidal vascular image from the fundus image; and
   the processor detecting a line passing through a macula and an optic nerve head in the choroidal vascular image as a watershed of a choroidal vascular network in the choroidal vascular image.

2. The image processing method of claim 1, wherein detecting the watershed includes the watershed being taken as a first watershed, and detecting a second watershed along a direction perpendicular the first watershed.

3. The image processing method of claim 2, wherein:
   the first watershed is along a horizontal line passing through the macula and the optic nerve head; and
   the second watershed is along a straight line orthogonal to the horizontal line and passing through the optic nerve head.

4. The image processing method of claim 1, wherein detecting the watershed of the choroidal vascular network includes:
   the processor detecting a position of an optic nerve head and a position of a macula in the choroidal vascular image.

5. The image processing method of claim 1, further comprising the processor dividing the fundus image into a plurality of areas with respect to the watershed.

6. The image processing method of claim 1, further comprising the processor displaying the watershed.

7. The image processing method of claim 1, further comprising the processor detecting a position of a vortex vein from the choroidal vascular image.

8. An image processing method comprising:
   a processor acquiring a fundus image;
   the processor generating a choroidal vascular image from the fundus image; and
   the processor detecting a watershed of a choroidal vascular network in the choroidal vascular image, wherein detecting the watershed of the choroidal vascular network comprises:
   the processor extracting the choroidal vascular network from the choroidal vascular image;
   the processor detecting a running direction of each choroidal blood vessel in the choroidal vascular network; and
   the processor detecting the watershed from the running direction of each of the choroidal blood vessels.

9. The image processing method of claim 8, further comprising the processor dividing the fundus image into a plurality of areas with respect to the watershed.

10. The image processing method of claim 8, further comprising the processor displaying the watershed.

11. The image processing method of claim 8, further comprising the processor detecting a position of a vortex vein from the choroidal vascular image.

12. An image processing method comprising:
    a processor acquiring a fundus image;
    the processor generating a choroidal vascular image from the fundus image; and
    the processor detecting a watershed of a choroidal vascular network in the choroidal vascular image, wherein detecting the watershed is detecting, as the watershed, an area of the choroidal vascular image having a lower density of choroidal blood vessels than other areas.

13. The image processing method of claim 12, further comprising the processor dividing the fundus image into a plurality of areas with respect to the watershed.

14. The image processing method of claim 12, further comprising the processor displaying the watershed.

15. The image processing method of claim 12, further comprising the processor detecting a position of a vortex vein from the choroidal vascular image.

16. An image processing device comprising:
    a memory; and
    a processor coupled to the memory,
    wherein the processor:
    acquires a fundus image;
    generates a choroidal vascular image from the fundus image; and detects a line passing through a macula and an optic nerve head in the choroidal vascular image as a watershed of a choroidal vascular network in the choroidal vascular image.

17. A non-transitory storage medium storing a program executable by a computer to perform image processing comprising:
acquiring a fundus image;
generating a choroidal vascular image from the fundus image; and
detecting a line passing through a macula and an optic nerve head in the choroidal vascular image as a watershed of a choroidal vascular network in the choroidal vascular image.

18. An image processing device comprising:
a memory; and
a processor coupled to the memory,
wherein the processor:
acquires a fundus image;
generates a choroidal vascular image from the fundus image; and
detects a watershed of a choroidal vascular network in the choroidal vascular image, and
detecting the watershed comprises:
extracting the choroidal vascular network from the choroidal vascular image;
detecting a running direction of each choroidal blood vessel in the choroidal vascular network; and
detecting the watershed from the running direction of each of the choroidal blood vessels.

19. A non-transitory storage medium storing a program executable by a computer to perform image processing comprising:
acquiring a fundus image;
generating a choroidal vascular image from the fundus image; and
detecting a watershed of a choroidal vascular network in the choroidal vascular image, and
detecting the watershed comprises:
extracting the choroidal vascular network from the choroidal vascular image;
detecting a running direction of each choroidal blood vessel in the choroidal vascular network; and
detecting the watershed from the running direction of each of the choroidal blood vessels.

20. An image processing device comprising:
a memory; and
a processor coupled to the memory,
wherein the processor:
acquires a fundus image;
generates a choroidal vascular image from the fundus image; and
detects a watershed of a choroidal vascular network in the choroidal vascular image, and
wherein detecting the watershed is detecting, as the watershed, an area of the choroidal vascular image having a lower density of choroidal blood vessels than other areas.

21. A non-transitory storage medium storing a program executable by a computer to perform image processing comprising:
acquiring a fundus image;
generating a choroidal vascular image from the fundus image; and
detecting a watershed of a choroidal vascular network in the choroidal vascular image, and
wherein detecting the watershed is detecting, as the watershed, an area of the choroidal vascular image having a lower density of choroidal blood vessels than other areas.

* * * * *